United States Patent [19]

Vestal et al.

[11] Patent Number: 4,861,989
[45] Date of Patent: Aug. 29, 1989

[54] ION VAPOR SOURCE FOR MASS SPECTROMETRY OF LIQUIDS

[75] Inventors: Marvin L. Vestal, Houston; Calvin R. Blakley, Kingwood, both of Tex.; Gordon J. Fergusson, Claremont, Calif.

[73] Assignee: Research Corporation Technologies, Inc., Tucson, Ariz.

[21] Appl. No.: 163,060

[22] Filed: Mar. 2, 1988

Related U.S. Application Data

[63] Continuation of Ser. No. 832,743, Feb. 24, 1986, Pat. No. 4,730,111, which is a continuation of Ser. No. 527,751, Aug. 30, 1983, abandoned.

[51] Int. Cl.$^4$ .............................................. B01D 59/44
[52] U.S. Cl. ..................................... 250/288; 250/281
[58] Field of Search ................... 250/281, 281, 423 R, 250/424, 425, 288, 288 A; 422/70; 436/161; 73/61.6 C

[56] References Cited

U.S. PATENT DOCUMENTS 2,712,073  6/1955  Martin .
(List continued on next page.)

FOREIGN PATENT DOCUMENTS

| 0153113 | 8/1985 | European Pat. Off. | ............. 250/282 |
|---|---|---|---|
| 0126241 | 10/1981 | Japan | ................................. 250/281 |
| 0101328 | 6/1982 | Japan | ................................. 250/288 |
| 08103394 | 11/1981 | PCT Int'l Appl. | ................. 250/288 |

OTHER PUBLICATIONS

Studies of Ionization Mechanisms Involved in Thermospray LC–MS.
Design and Performance of a Simplified LC–MS Using the Thermospray Technique.
Ion Emissions from Liquids.
Vestec Corporation, Thermospray LC–MS Kits and Interfaces the first sale of applicants device.
Amino Acids Sequence of Polypeptides by Enzymatic Hydrolysis and Direct Detection Using a Thermospray LC–MS.
Mass Spectrometry Reviews.
"LC/MS Coupling" by Arpino and Guiothon *Analytical Chemistry*, vol. 51, No. 7, Jun. 1979.
"Thermospray Interface for Liquid Chromatography/Mass Spectrometry," by Blakley and Vestal, American Chemical Society, 1983.

*Primary Examiner*—Janice A. Howell
*Assistant Examiner*—Michael Arnoff
*Attorney, Agent, or Firm*—Scully, Scott, Murphy & Presser

[57] ABSTRACT

This disclosure is concerned with method and apparatus for vaporizing liquid solutions in order to detect, quantitate, and/or determine physical or chemical properties of samples present in liquid solution. Mixtures may be separated by an on-line liquid chromatographic column and the methods used for detection, quantitation, indentification, and/or determination of chemical and physical properties include mass spectrometry, photoionization, flame ionization, electron capture, optical photometry, including UV, visible, and IR regions of the spectrum, light scattering, light emission, atomic absorption, and any other technique suitable for detecting or analyzing molecules or particles in a gaseous or vacuum environment. The method and apparatus involves controlled partial vaporization of the solution. Methods are disclosed for controlling the degree of partial vaporization and the temperature at which this vaporization occurs, and for maintaining this degree of vaporization essentially constant even though the solvent flow rate and/or composition may vary in either a controlled or an uncontrolled fashion. This "thermospray" method and apparatus allows the solvent to be substantially vaporized to produce supersonic free jet containing a fraction of unvaporized solvent as liquid droplets entrained in the jet. Solutes which are less volatile than the solvent are preferentially contained in the droplets. Methods are disclosed for controlling the temperature at which this process occurs in order to prevent unwanted chemical modification of the solutes (for exmaple, pyrolysis) and to prevent premature vaporization of the solutes.

20 Claims, 19 Drawing Sheets

U.S. PATENT DOCUMENTS

| | | |
|---|---|---|
| 2,715,186 | 8/1955 | Hull et al. . |
| 2,717,962 | 9/1955 | Wouters . |
| 2,727,151 | 12/1955 | Parkins . |
| 2,789,229 | 4/1957 | Lawrence . |
| 2,824,967 | 2/1958 | Kamen . |
| 2,978,580 | 4/1961 | Von Ardene . |
| 3,229,409 | 1/1966 | Johnson . |
| 3,299,409 | 1/1966 | Johnson ................................ 43/129 |
| 3,449,563 | 6/1969 | Brown . |
| 3,458,699 | 7/1969 | Padrta . |
| 3,560,627 | 2/1971 | Langer . |
| 3,697,748 | 10/1972 | Cohen . |
| 3,751,660 | 8/1973 | Thurston . |
| 3,801,788 | 4/1974 | Milne . |
| 3,841,146 | 11/1974 | Bennett ................................ 19/300 |
| 3,851,146 | 11/1974 | Bennett . |
| 3,888,107 | 6/1975 | Langer et al. . |
| 3,896,661 | 7/1975 | Parkhurst et al. . |
| 3,943,363 | 3/1976 | Amblard . |
| 3,997,298 | 12/1976 | McLafferty et al. . |
| 4,024,217 | 5/1977 | Wexler et al. . |
| 4,055,987 | 11/1977 | McFadden . |
| 4,066,409 | 1/1978 | Fine ................................ 23/230 PC |
| 4,112,297 | 9/1978 | Miyagi et al. . |
| 4,122,343 | 10/1978 | Rizbe et al. . |
| 4,140,905 | 2/1979 | Polanyi . |
| 4,156,814 | 5/1979 | Hunt et al. . |
| 4,160,161 | 7/1979 | Horton ................................ 250/281 |
| 4,178,507 | 12/1979 | Brunnee et al. . |
| 4,197,455 | 4/1980 | Blanchard et al. ................. 250/288 |
| 4,209,696 | 6/1980 | Fite ..................... 250/281 |
| 4,239,967 | 12/1980 | Carr et al. . |
| 4,281,246 | 7/1981 | White et al. ............................. 59/44 |
| 4,298,795 | 11/1981 | Takeuchi et al. ................... 250/288 |
| 4,300,044 | 11/1981 | Iribarne et al. . |
| 4,403,147 | 9/1983 | Melerz et al. ........................ 250/288 |
| 4,531,056 | 7/1985 | Labonski et al. ................... 250/288 |
| 4,590,371 | 5/1986 | Ottley ................................ 250/289 |
| 4,647,772 | 3/1987 | Lewis et al. ......................... 250/288 |

ION VAPOR SOURCE FOR MASS SPECTROMETRY OF LIQUIDS

GOVERNMENT SUPPORT

The invention described herein was made in the course of work under a grant or award from the Department of Health, Education, and Welfare.

CROSS-REFERENCE TO RELATED APPLICATIONS

This application is a continuation of our prior application U.S. Ser. No. 832,743, filed Feb. 24, 1986 entitled "ION VAPOR SOURCE FOR MASS SPECTROMETRY OF LIQUIDS," now U.S. Pat. No. 4,730,111, which is a continuation of our prior application U.S. Ser. No. 527,751 filed Aug. 30, 1983 entitled "Ion Vapor Source for Mass Spectrometry of Liquids," now abandoned the entire disclosure of which is incorporated herein by reference thereto.

BACKGROUND OF THE INVENTION

The information in the mass spectrum of a chemical compound is of great value to chemists in identifying the compound and in characterizing its molecular structure. For those compounds for which mass spectra can be obtained, the mass spectrum typically reveals the molecular weight of the compound and the masses of a characteristic assortment of ionic fragments derived from the compound. To generate mass spectra, conventional mass spectrometers operate on a beam of ions derived from the material to be analyzed, either by deflecting the beam electromagnetically in a way which depends upon the ratio of the mass to the charge of the ions in the beam, or by measuring transit times of ions in a pulsed ion beam. Compounds which are to be mass analyzed generally must be converted into an ion vapor before introduction into the section of a conventional mass spectrometer which forms the ion beam.

The need to convert materials to be mass analyzed into an ion vapor has been a source of problems in the field of mass spectrometry for which no completely satisfactory solution has heretofore existed. Gaseous compounds or compounds which can be thermally vaporized without decomposition can usually be converted to an ion vapor relatively easily by heating the compound to vaporize it if it is not a gas, and either bombarding the compound in the gaseous state with a beam of electrons (electron impact ionization) or by introducing chemically-reactive ions into the gas (chemical ionization). However, many compounds are not sufficiently volatile at ambient temperatures to form a gas suitable for either electron-impact ionization or chemical ionization, and moreover, decompose when heated so that they cannot be vaporized thermally. Among the compounds which cannot be converted into an ion vapor by these conventional techniques are many which are of biological, medical and pharmaceutical interest.

A number of special techniques have been developed to generate an ion vapor from compounds of low volatility. These techniques include field desorption, laser-assisted field desorption, plasma desorption, rapid evaporation from inert surfaces, and secondary ionization mass spectrometry. Literature citations to these and other techniques may be found in *Analytical Chemistry*, vol 52, pp. 1589A-1606 (Dec. 1980). None of these techniques is without its limitations, however, and a need still exists for improved methods for obtaining mass spectra of involatile, heat-sensitive materials. The problems of forming an ion vapor of involatile and heat-sensitive compounds become particularly acute when it is attempted to use a mass spectrometer to analyze the effluent of a liquid chromotograph. Liquid chromotographs are widely used to separate mixtures into their component compounds, and find particular application when one or more of the component compounds is too involatile to permit the mixture to be separated with a conventional gas chromotograph. Although mass spectrometers have been widely and successfully interfaced to gas chromatographs to permit mass spectra to be taken of compounds in the gaseous effluent from the chromatograph, efforts to interface liquid chromatographs to mass spectrometers have been less successful, in part because compounds eluted from the liquid chromatograph are frequently involatile and heat sensitive and thus not amenable to conversion into an ion vapor by conventional techniques. Moreover, the compounds to be analyzed from the liquid chromotograph are dissolved in a volatile solvent, which tends to reduce the ionization efficiency of the mass spectrometer even further with respect to the solute compounds of interest since solvent vapor is generally ionized along with the solute compounds and the solvent is typically in a much greater concentration than the solute compounds.

During the past decade several laboratories have worked on the development of combined liquid chromatograph-mass spectrometer systems. Much of this work has focused on dealing with the fact that the mass flows involved in conventional high pressure liquid chromatography (ca. 1 g/min) are two or three orders of magnitude larger than can be accommodated by conventional mass spectrometer vacuum systems. The status of various approaches to overcoming the apparent incompatibility between liquid chromatography and mass spectrometry has recently been summarized by P. J. Arpino in Trends in Anal. Chem. 1, 154 (1982) and Biomed. Mass Spectrum 9 176 (1982).

An early approach to LC-MS employed laser heating to rapidly vaporize both the solvent and sample and molecular beam techniques to transport and ionize the sample while minimizing contact of the sample molecules with solid surfaces. This apparatus used a large and expensive vacuum system and a 50 watt $CO_2$ laser. Later, a greatly simplified version on this system used oxy-hydrogen flames to vaporize the LC effluent and a substantially less elaborate vacuum system. This system is described in an article by C. R. Blakely, J. J. Carmody and M. L. Vestal in Anal. Chem. 52 1636 (1980).

Earlier systems were designed to efficiently transfer the sample to either an electron impact (EI) or chemical ionization (CI) source while vaporizing and removing most of the solvent. In the latter version more than 50% of the sample was transferred to the CI ion source with only about 5% of the solvent vapor. This system gave satisfactory performance for a number of relatively nonvolatile samples and was used successfully with reversed phase separations employing aqueous buffers at flow rates as high as 1 ml/min. The major problem with this system was that the vaporizer was difficult to control properly which often caused uncontrolled fluctuations in performance and some times frustrated attempts at application of the system to real analytical problems.

In the course of this work it was found that, under certain conditions, ions were produced even though the hot filament normally used to produce the primary ionizing beam was turned off. Initial measurements of mass spectra produced from nonvolatile compounds such as peptides, nucleosides, and nucleotides, showed that the spectra were quite different from those obtained by chemical ionization and were, in fact, most similar to those obtained by field desorption.

SUMMARY OF THE INVENTION

The present invention is concerned with methods and apparatus for vaporizing liquid solutions in order to detect, quantitate, and/or determine physical or chemical properties of samples present in liquid solution. Mixtures may be separated by an on-line liquid chromatographic column and the methods used for detection, quantitation, identification, and/or determination of chemical and physical properties include mass spectrometry, photoionization, flame ionization, electron capture, optical photometry including UV, visible, and IR regions of the spectrum, light scattering, light emission, atomic absorption, and any other technique suitable for detecting or analyzing molecules or particles in a gaseous or vacuum environment. The novel method consists of a two-step process. The first step is controlled partial vaporization of the solution. Methods are disclosed for controlling the degree of partial vaporization and the temperature at which this vaporization occurs, and for maintaining this degree of vaporization essentially constant even though the solvent flow rate and/or composition may vary in either a controlled or an uncontrolled fashion. This "thermospray" method allows the solvent to be substantially vaporized to produce a supersonic free jet containing a fraction of unvaporized solvent as liquid droplets entrained in the jet. Solutes which are less volatile than the solvent are preferentially contained in the droplets. Methods are disclosed for controlling the temperature at which this process occurs in order to prevent unwanted chemical modification of the solutes (for example, pyrolysis) and to prevent premature vaporization of the solutes.

Several different methods may be used for the second stage of the vaporization depending on the application and the characteristics of the analytical technique to be employed. Conditions may be chosen in the first stage so that the droplets or particles produced are accelerated to high velocities, in some cases even exceeding the local velocity of sound. Depending on the application, these droplets or particles may be further vaporized by interaction with heated vapor or gas; they may be directed onto a relatively cool surface where the less volatile components will stick while the remainder of the solvent and any volatile components are vaporized; or they may be caused to impact on a heated surface at high velocity causing them to shatter into smaller droplets or to vaporize. Methods are disclosed for separating the sample particles from some or substantially all of the solvent vapor prior to significant vaporization. In some cases the samples may be analyzed as solids deposited on a surface, in others they may be revaporized in a subsequent step for analysis by a gas phase technique. Method and apparatus are disclosed for producing a high velocity beam of particles or nonvolatile molecules which may be analyzed by techniques suitable for studying such beams in a vacuum.

The present invention uses an electrically heated vaporizer which allows more precise control of the solvent vaporization. The present version allows the stable vaporization of virtually any solvent including aqueous buffers at flow rates up to at least 2 ml/min. The use of this electrically heated vaporizer has greatly improved the stability and reproducibility of the vaporization of solvents and nonvolatile samples and it is now possible to predict with confidence the conditions appropriate for a particular solvent composition and flow rate. The availability of a stable, reproducible vaporizer has also allowed more definitive studies of the vaporization and ionization mechanisms to be conducted. The results of these studies have led to some further modifications of the apparatus which both improve the performance and further simplify the construction. The present invention may be readily adapted to any commercial quadrupole mass spectrometer equipped with a vacuum system suitable for CI operation. The only addition to the vacuum system is a single stage mechanical vacuum pump of moderate capacity (ca. 300 l/min.). It now appears that the apparent incompatibility between LC and MS has been successfully overcome and that a truly practical LC-MS has been developed.

DETAILED DESCRIPTION OF THE PREFERRED EMBODIMENT

Figure 1:
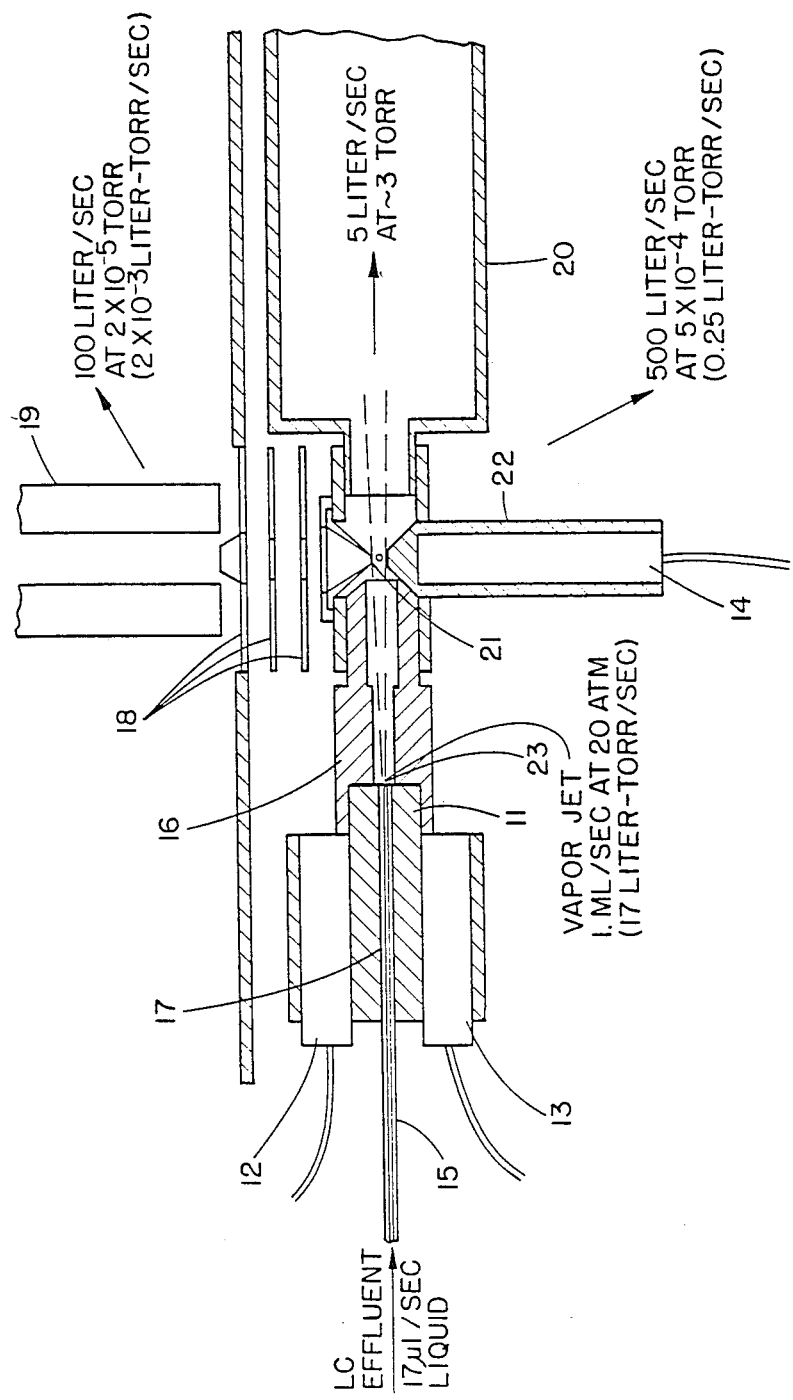
FIG. 1 is a diagrammatic and partially cross sectional view of a first embodiment of the invention.

The thermospray method allows controlled vaporization of solutions in such a way that the chemical nature of solutes is not changed by the process even though they may be nonvolatile, ionic, or thermally labile. The technique was originally developed as a means of coupling liquid chromatography to mass spectrometry, but is has a variety of other potential applications.

It is common in a number of analytical situations that the analyte is in the form of a liquid solution. In some cases (e.g. near UV and visible photometry) the solute can be detected and analyzed in solution since the properties of the solvent may be sufficiently different from those of the solute so as not to interfere with the measurement. In other cases, either because of solvent interference or because the analytical method (for example, mass spectrometry) is a gas phase technique, it is necessary to vaporize the solution. Since the solvent is usually not of direct interest and also because it may interfere in some way with the desired measurement, it is often necessary or desirable to vaporize the solution in such a way that some, or substantially all, of the solvent is separated from the solute or solutes of interest. It is also very important in many cases that the solute not be chemically modified (for example, by pyrolysis) as a result of the vaporization process. Whether or not the solvent is removed preferentially, it is important that the solute be efficiently transferred to the analytical instrument if high sensitivity is to be achieved. Up to now there has been no practical way of accomplishing the desired performance, particularly when the sample is a nonvolatile and/or thermally labile substance in an aqueous solution. The thermospray technique is particularly well-suited for these most demanding applications, but also provides a simple, economical, and efficient vaporization technique for many less difficult cases.

The most important component of the thermospray system is the vaporizer with its associated control system. This device provides controlled partial vaporization of liquid streams containing solutes which may be nonvolatile, ionic, and/or thermally labile. A supersonic jet of vapor is produced which contains entrained liquid droplets and/or solid particles. Samples whose volatility is less than that of the solvent are preferentially contained in these droplets or particles. Method and apparatus are disclosed both for accomplishing the desired degree of vaporization of the liquid stream and for controlling the vaporizer so that this desired degree of partial vaporization is achieved even though the solvent composition or flow rate may vary.

In some cases the thermospray vaporizer may be combined directly with well-known analytical techniques to achieve useful results, but in others it is necessary to provide additional control over the temperature and pressure of the environment surrounding the supersonic jet and downstream of the Mach disk to achieve the desired results. This downstream control system is particularly important in the application to direct LC-MS coupling both for analysis of neutral molecules and for direct controlled vaporization of molecular ions from electrically charged droplets and particles. Details of the individual components and combinations into complete systems for various applications are described below.

1. Thermospray Vaporizer and Control System

The basic element of the thermospray vaporizer is a small diameter tube through which liquid is forced at essentially constant flow rate, for example, by the kinds of pumps typically used in high pressure liquid chromatography. Depending on the application, the end of this tube may be in gas (for example air) at atmospheric pressure (or higher) or may be in a substantially reduced pressure environment. To produce the thermospray jet is is necessary to heat the tube at or near the end sufficiently to produce the desired degree of vaporization. In earlier work vaporization was produced by heating the end of the tube with a $CO_2$ laser or with an oxyhydrogen flame. Neither of these techniques was entirely satisfactory since they were difficult to control and required that the tube be heated in a rather small region to rather high temperatures to achieve the required heat input. More recently second embodiments of the electrically heated vaporizers were developed for this purpose. A schematic diagram of the "thermospray" system presently in use is illustrated in FIG. 1. This interface and ion source are much simpler than the earlier versions and requires only minor modification of a commercial quadrupole mass spectrometer. This version of the vaporizer consists of a few centimeters of 0.015 mm ID by 1.5 mm OD stainless steel tubing which is brazed at one end into a copper block. The block is heated by two commercial 100 watt cartridge heaters normally operated at substantially below their rated power. A thermocouple is imbedded in the copper block to monitor the temperature of the vaporizer and may be used in conjunction with a proportioning controller to maintain the temperature of the block constant. The length of tubing immersed in the block is not particularly critical, but lengths on the order of 3 cm are suitable. It is very important that the stainless tube be in good thermal contact with the copper block; the brazed joint is essential.

As illustrated in FIG. 1, the thermospray apparatus uses an electrically heated vaporizer block 11, and two 100 watt cartridge heaters 12, 13 and 14. The copper block 11, is brazed at 17 to stainless steel capillary 15; 1.5 mm OD×0.15 mm ID stainless steel capillary tube. The vaporizer also includes a thick-walled copper tube 16 which is mounted adjacent the input of a quadrupole mass spectrometer. The mass spectrometer is illustrated schematically in FIG. 1, with ion lenses 18, the quadrupole mass filter 19, a pump out line 20 to a mechanical pump (not shown in FIG. 1); an ion exit aperture 21; and source heater 22.

In operation, on the order of 17 ml per second of liquid is vaporized to produce a vapor jet at an initial pressure of approximately 20 atmospheres plus (17 liter-torr/sec). The pump out line 20 is pumped by a mechanical pump to maintain an effective pressure in the ion source of approximately 3 torr. The mass spectrometer 19 is pumped at approximately 100 liter per second to maintain an effective pressure within the spectrometer of less than $2 \times 10^{-5}$ torr. The ambient atmosphere evacuated from the region adjacent the entrance to the mass spectrometer at a rate of approximately 500 liters per second to maintain an effective pressure of approximately $5 \times 10^{-4}$ torr.

The vaporizer produces a supersonic jet of vapor 23, normally containing a mist of fine particles or droplets. This jet traverses the ion source of the mass spectrometer and enters directly into a 1 cm dia pumping line 20, which is connected to a 300 l/min mechanical vacuum pump. Modifications to the ion source include the use of a conical ion exit aperture 21 (as shown in FIG. 1) and high capacity source heater 22 consisting of an 100 watt cartridge heater 14 imbedded in a copper rod which extends into the ion source cavity but does not intersect the main part of the jet. Except for the vaporizer, pump-out line 20 and source block 22 the thermospray LC-MS system illustrated in FIG. 1 is a commercial quadrupole mass spectrometer equipped for CI operation.

At first it is somewhat surprising that this system can accommodate vaporizing up to 2 ml/min of liquid directly into the ion source without overloading the pumping systems since this corresponds to a gas flow which is about 100 times larger than that used with the mass spectrometer operated in the conventional CI mode. The addition of the mechanical vacuum pump connected directly to the source would only account for about one order of magnitude of increased capacity normally, but locating the pumping line directly opposite the thermospray vaporizer allows the supersonic jet to act as its own ejector pump. Thus the conductance of the pumping aperture is about ten times as high as normal due to highly directed flow of the jet. We have found that a 300 l/min mechanical pump is more than adequate to maintain stable performance at flow rates to 2 ml/min. It is essential that the pump be operated with gas ballast to avoid excess accumulation of liquid in the pump oil. Even then, it is important to service the pump frequently (usually daily) to drain out solvent and add pumping fluid.

DESIGN AND PERFORMANCE OF THE FIRST EMBODIMENT

The maximum velocity with which a superheated liquid may vaporize is given by $$v_v = \left(\frac{m}{2\pi kT}\right)^{\frac{1}{2}} \frac{P_v(T)}{\rho L} \quad (1)$$

where $P_v(T)$ is the vapor pressure at temperature T, m is the molecular mass, $\rho$ is the density of the liquid, k the Boltzmann constant, and L is Avogadro's number. For steady vaporization from the capillary nozzle the vaporization velocity given by (1) must be equal to the velocity of the liquid flow in the capillary tube. Assuming that sufficient heat is supplied, the temperature of the vapor emerging from a given diameter capillary nozzle is determined by (1) and the liquid flow rate.

Figure 2:
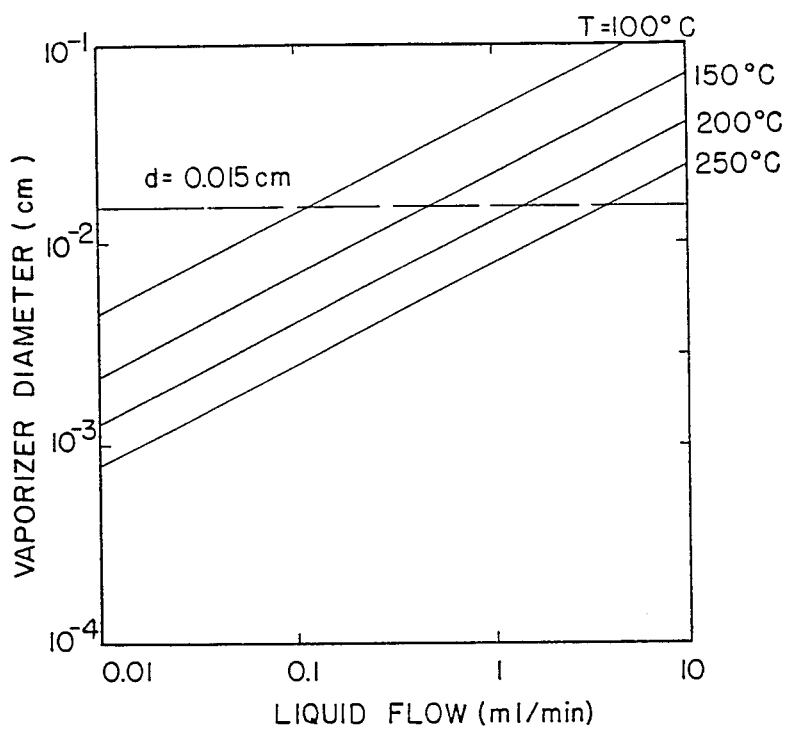
FIG. 2 is a graph illustrating the temperature of water vapor emerging from a given diameter capillary nozzle as a function of the liquid flow rate.
Figure 4:
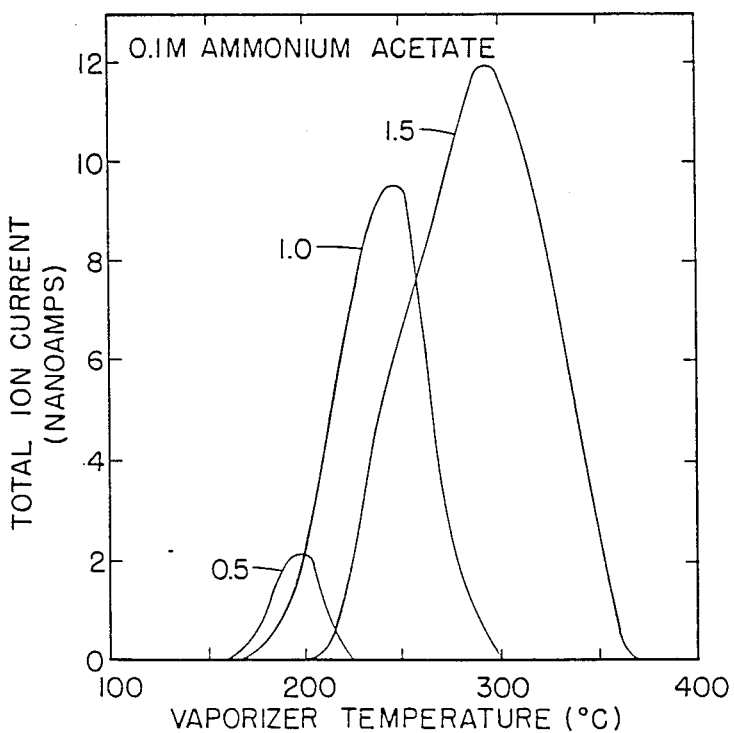
FIG. 4 is a graph illustrating the total ion currents that may be obtained from thermospray ionization of 0.1M aqueous ammonium acetate, measured as a function of vaporizer temperature and flow rate.

This relationship is illustrated for water vapor in FIG. 2. This Figure illustrates the relationship between vaporizer diameter and liquid flow rate for steady vaporization of water at the indicated vapor temperatures. The horizontal dashed line corresponds to the capillary nozzle used in the present work and the intersection with the isotherms gives the expected flow rate for steady vaporization at that temperature. At a flow rate of 1.0 ml/min of water through the 0.015 cm ID capillary illustrated in FIG. 1, steady vaporization produces vapor at approximately 183° C. and at a pressure of about 10.5 atm. Measurement of liquid pressures and temperatures in the jet confirm that the behavior is approximately as predicted by the model.

In the thermospray vaporizer the temperature of the copper block coupling the heaters to the stainless steel capillary is monitored by a thermocouple (not shown in FIG. 1). For stable operation is essential that good thermal contact be maintained between the copper block and the capillary; this is accomplished by brazing them together at 17 using a suitable silver alloy. The heat transfer from the copper block to the flowing fluid is then determined almost entirely by the temperature drop in the capillary tubing and at the solid liquid interface. If the temperature were uniform over the length of the vaporizer, L, then for the cylindrical geometry used the resistance to heat flow is given by $$R = \frac{1}{2\pi L}\left[\frac{\ln(b/a)}{k_s} + \frac{2}{nk_f}\right]$$

where a and b are the inner and outer diameter, respectively, of the capillary tube; $k_s$ is the thermal conductivity of the stainless steel tube ($k_s = 0.16$ w/cm °C.) and $k_f$ is the thermal conductivity of the liquid (for water $k_f = 6 \times 10^{-3}$ w/cm °C.) n is the Nusselt number for the liquid solid interface. Equation (2) is an approximation to the actual case because, while the temperature of the outer surface is essentially constant over the length of the vaporizer, the temperature of the fluid varies along the length from that of the liquid at ambient to that of the vapor at the exit. In any case the heat flow, h, is related to the temperature drop between the copper block and the fluid by an equation of the form $$h = (T - T_f)/R \quad (3)$$

where T is the temperature of the copper block and $T_f$ is the average temperature of the fluid in the vaporizer which we approximate by the arithmetic mean between the entrance and exit temperatures. If just enough heat is supplied to completely vaporize the liquid as is passes through the vaporizer, then the total heat transferred must be equal to the heat required to convert liquid to vapor at the exit temperature and pressure.

If the temperature of the heater is higher than the minimum required for steady vaporization, then the necessary heat can be supplied in a length shorter than the length of the heater and vaporization will tend to occur inside the capillary; on the other hand, if insufficient heat is supplied, superheated liquid will emerge and begin to vaporize only after exiting the capillary. From correlation of visual observation of the vaporizer jet in the laboratory with the behavior of the vaporizer installed in the mass spectrometer, it appears that the best performance probably corresponds to nearly complete vaporization occurring a short distance back inside the vaporizer. Since heat is supplied to the liquid primarily by conduction from the walls, the vaporization of the liquid near the axis of the capillary will tend to lag behind that near the walls. If the nominal liquid-vapor interface is near the exit of the vaporizer, this portion of the liquid emerges as a visible mist entrained in the vapor jet. At slightly higher vaporizer temperatures the mist disappears and a hot, dry, very intense vapor jet emerges from the capillary, presumably with sonic velocity at the exit.

The vaporizer temperature for the best performance in the mass spectrometer corresponds, in the laboratory atmosphere, to the production of a jet containing visible, very fine droplets which produce a visible spot upon striking a room temperature surface but which vaporize on impact leaving no accumulation of liquid on the surface. The vaporizer temperature at which this behavior is observed for water is plotted as a function of flow rate in FIG. 3, where it is compared with the calculated vapor temperature using the steady vaporization model.

Figure 3:
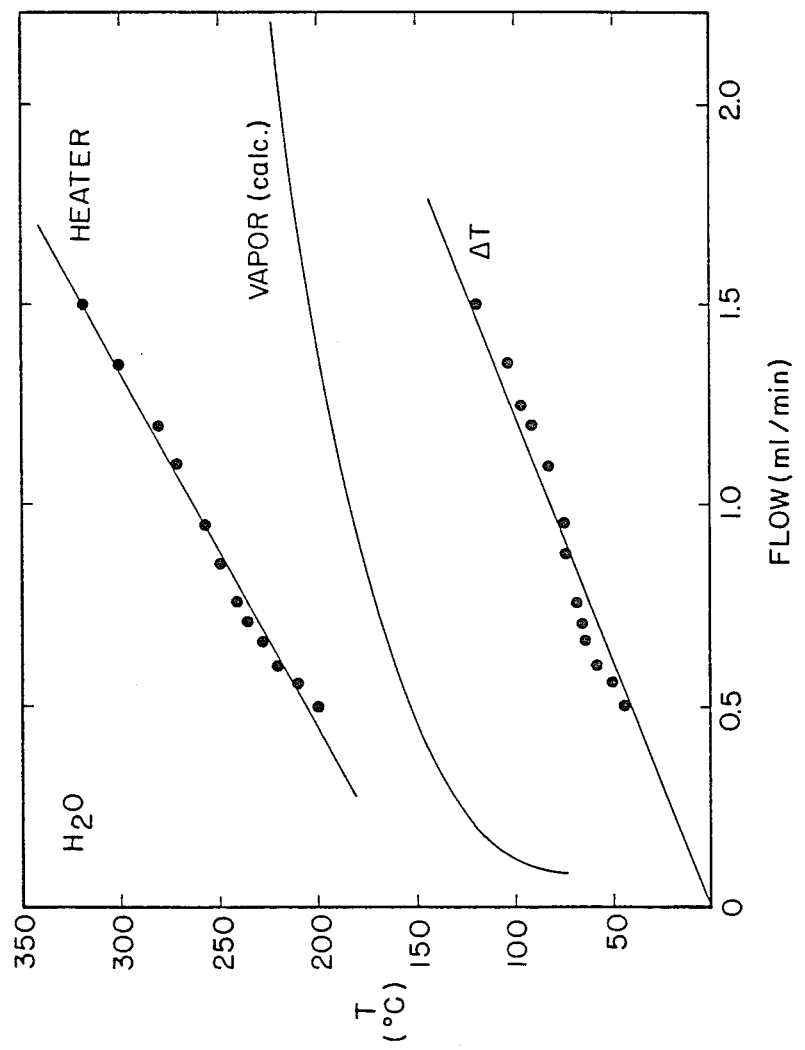
FIG. 3 is a graph illustrating the relationship between temperature and flow rate for the vaporizer heater temperature, the calculated vapor temperature and $\Delta T$, the difference between the vaporizer temperature and calculated vapor temperature.
Figure 5:
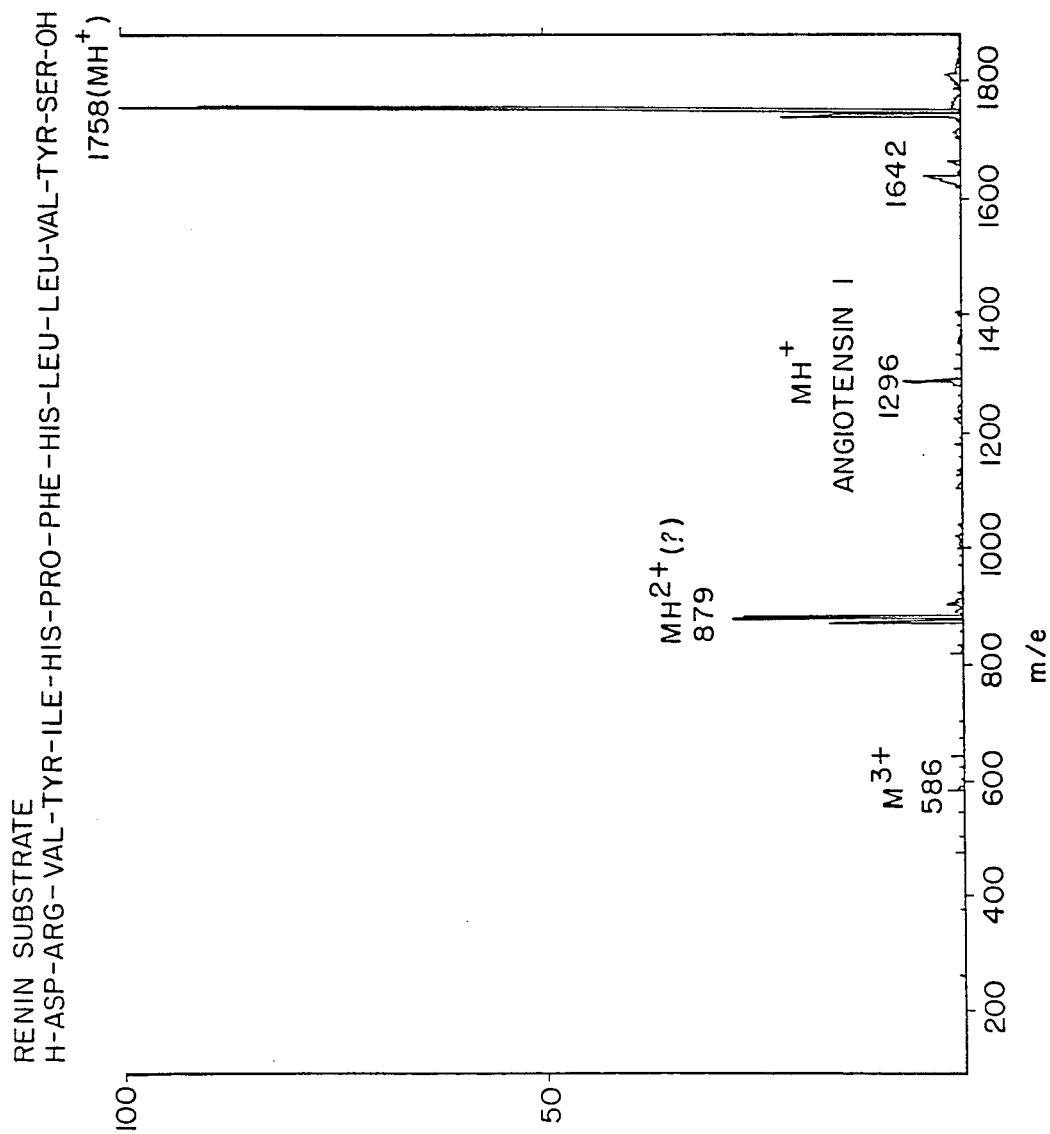
FIG. 5 is a mass spectrum of a tetradecapeptide renin substrate.

In FIG. 3 the upper curve (heater) gives the measured temperature of the vaporizer heater block required to produce a fine dry mist when thermospraying water in the laboratory atmosphere. The middle curve gives the calculated vapor temperature according to the steady vaporization model for the 0.015 cm dia capillary used in this work. The lower curve (T) is the difference between the upper and middle curves and corresponds to the temperature drop in the stainless steel capillary and the solid-liquid interface. Also shown in FIG. 3 is the difference between the vaporizer temperature and the calculated vapor temperature This difference is approximately proportional to the flow rate. If it is assumed that the temperature of the liquid entering the vaporizer is about 30° C., these results correspond to a thermal resistance of about 3.2° C./watt. The resistance corresponds to a value of the convection coefficient, n, in equation (2) of ca. 7 which implies that about 80% of the thermal resistance is due to the solid-liquid interface. With the thermal resistance of the vaporizer known, the vaporizer temperature necessary to produce steady vaporization of any liquid can readily be calculated.

The efficiency of thermospray ionization is very sensitive to vaporizer conditions. Total ion currents obtained from thermospray ionization of 0.1M aqueous ammonium acetate measured as a function of vaporizer temperature and flow rate are summarized in FIG. 4.

FIG. 4, illustrates the total ion current produced by thermospray ionization of 0.1M aqueous ammonium acetate as function of vaporizer temperature. The flow rates in ml/min are as indicated. These results were obtained by operating the quadrupole with only RF excitation so as to transmit all of the ions and by collecting the ions on a Faraday cup at the quad exit. No external source of ionization was used for these experiments and no electrical fields were employed inside the ion source. These results were obtained for positive ions, but approximately equal intensities of negative ions are also produced and their behavior with temperature and flow rate is similar.

These results correlates well with visual observations. The maximum current corresponds to production of a relatively dry mist in an intense vapor jet; the temperatures corresponding to the maxima in FIG. 4 are in excellent agreement with the optimum temperature vs. flow rate results obtained visually (FIG. 3). Also the temperature at which the current vanishes on the high temperature side correlates with disappearance of the mist while the low temperature threshold for current production correlates with the minimum temperature for jet formation. Mass spectra obtained by thermospray ionization of aqueous ammonium acetate show that the positive ion spectra consist almost entirely of $NH_4^+$ and its clusters with water, ammonia, and acetic acid while the negative ion spectra consists of the acetate ion clustered with one or two acetic acid molecules. Approximately equal total intensities of positive and negative ions are observed. If the ionic strength of the solution is less than about $10^{-3}$ molar, the ion current is weak; at higher ionic strength (up to 3M) the ion current is proportional to the square root of the concentration of ions in solution. The ion current is strongly dependent on the liquid flow rate and vaporizer temperature. For example, for 0.1M ammonium acetate at 1 ml/min the ion current maximizes at a vaporizer temperature of about 250° C.; the current vanishes at vaporizer temperatures below 170° C. and above 300° C.

Intact molecular ions are observed for large nonvolatile molecules which are ionized in solution. Examples include peptides such as the tetradecapeptide renin substrate, vitamin $B_{12}$, and several dinucleotides. Multiply charged ions are sometimes observed for large molecules which may be multiply charged in solution, but multiply charged ions have not been observed for small multiply charged inorganic ions. Many molecules which are neutral in solution have been observed as either $M+H^+$ or $M-H^-$ ions in the mass spectrum, sometimes with high ionization efficiency. Fragment ions are sometimes observed, but neither $M^+$ nor $M^-$ ions have been observed for any of the several hundred molecules studied to date.

Studies of the mechanism of thermospray ionization are still in progress, but the major features are now fairly well understood.

(1) Briefly, it appears that the process begins with nearly complete vaporization of the liquid at the rate which it is supplied to the vaporizer to produce a superheated mist carried in a supersonic jet of vapor. Nonvolatile molecules are preferentially retained in the droplets of the mist.

(2) The droplets of the mist are charged positively or negatively according to statistical expectations for random sampling of a neutral fluid containing discrete positive and negative charges.

(3) Molecular ions clustered with a few solvent molecules evaporate from the superheated droplets assisted by the high local electrical fields generated by the charge on the droplet.

(4) The initially formed cluster ions rapidly equilibrate with the vapor in the ion source to produce the degree of solvation appropriate to the temperature and pressure of the vapor in the source. Ion-molecule reactions will occur if exothermic channels are available.

(5) Finally, the ions present in the source diffuse to the sampling aperture and are transmitted to the mass analyzer. While some details of this proposed mechanism remain somewhat speculative at present, all of the observations to date are compatible with it.

Thermospray ionization appears to provide intact molecular ions for any molecule which is ionized in solution and the efficiency of producing these ions seems nearly independent of the molecular weight and volatility of sample. As an example, a spectrum of the tetradecapeptide renin substrate is shown in FIG. 5.

This is the largest molecule which has been successfully detected using thermospray ionization to date and is near the upper mass limit of the quadrupole as presently configured. The mass resolution is too low and the mass scale calibration too uncertain in this high range to assign with certainty the peaks corresponding approximately to doubly and triply charged ions. From recent results on field desorption of large peptides with multiply ionizable side chains, (12) it is tentatively suggested that these are probably doubly and triply protonated molecules. Similar results have been obtained on other molecules with molecular weights in excess of 1000 amu including vitamin $B_{12}$, grammicidin, and several peptides. FIG. 5 illustrates a thermospray ionization mass spectrum of renin substrate obtained from 10 microgram injected into 0.1M ammonium acetate flowing at 1 ml/min. The peak at m/e 1296 is tentatively identified as due to angiotensin I present as an impurity in the sample while the peaks at approximately 879 and 586 are probably due to multiply protonated molecules.

Most of the recent work on applying the thermospray system to analyses by LC-MS has focused on reversed phase chromatography using ammonium acetate buffer with either methanol or acetonitrile as organic modifer with flow rates between 1 and 2 ml/min. An example of a chromatograph obtained on a test mixture is shown in FIG. 6.

Figure 6:
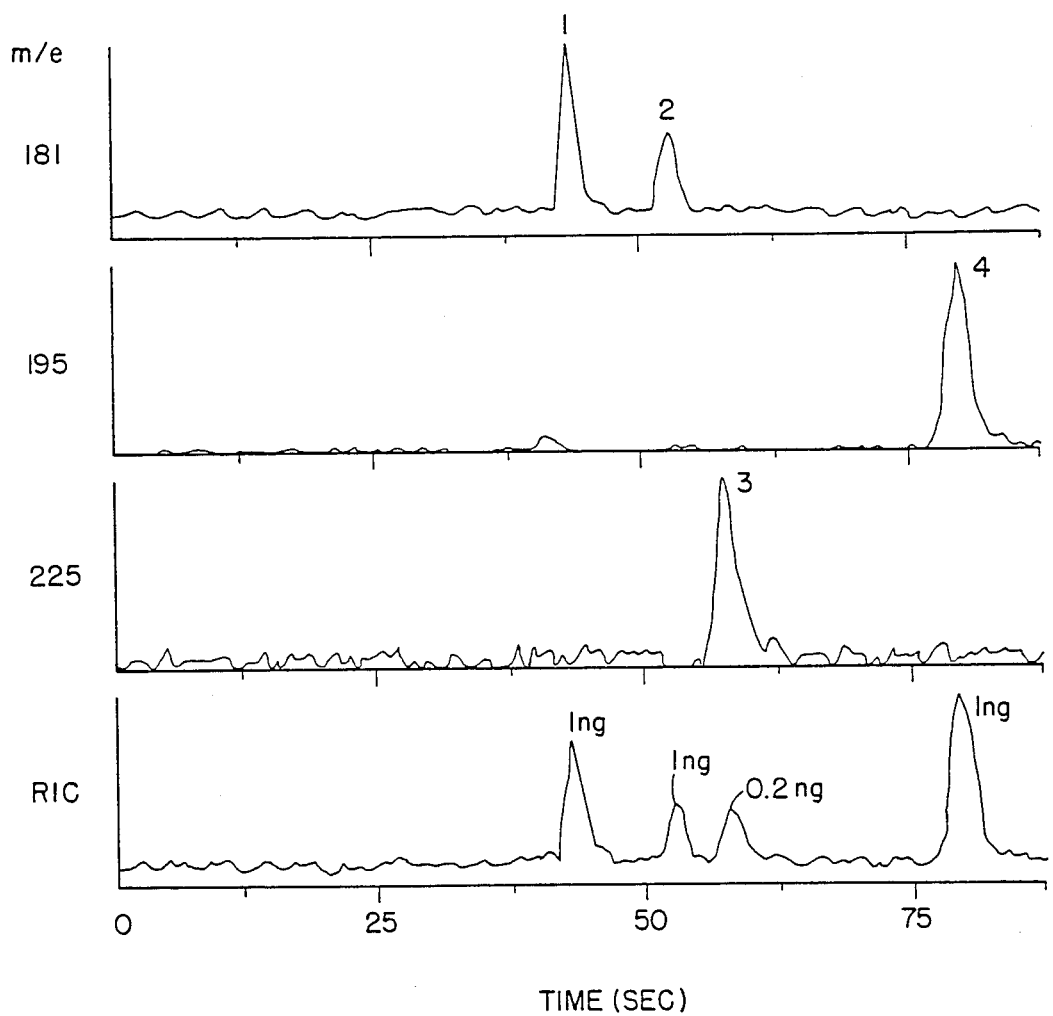
FIG. 6 is a chromatograph of a test mixture wherein the present invention was applied to reversed phase chromatography.

FIG. 6 illustrates LC-MS analysis of a mixture of xanthine derivatives; 1, theobromine; 2, theophylline, 3, β-hydroxyethyltheophylline; 4, caffeine. The LC figures were obtained using a 3 μm Ultrasphere (Altex) ODS column and mobile phase consisting of 12% acetonitrile in 0.1M ammonium acetate at flow rate of 1.5 ml/min. The mass spectra was obtained using thermospray ionization of the total liquid chromatography effluent. The sample quantities are indicated on the figure.

Several features of the performance of the system are illustrated by these results. The response is quite dependent of the properties of the sample molecule, and it is not yet possible to predict reliably the relative response of similar molecules. For example, the sentivity for β-hydroxyethyltheophylline is about five times that for theophylline.

The peaks in the chromatogram shown in FIG. 6 are between 2 and 3 seconds wide FWHM; the caffeine peak corresponds to an overall efficiency of about $10^4$ theoretical plates. Any contribution to band broadening by the mass spectrometer is undetectable. Regular oscillations in the background intensity, for example at m/e 181, which occurs with a period of about 3.5 seconds are due to flow fluctuations introduced by the HPLC pump. These oscillations in flow are only about 2% of the nominal flow but because of the strong dependence of ion intensities on liquid flow rate these oscillations are amplified to about 20% in the signal. At present this oscillation due to flow fluctuation is primarily responsible for setting the noise level.

Figure 7:
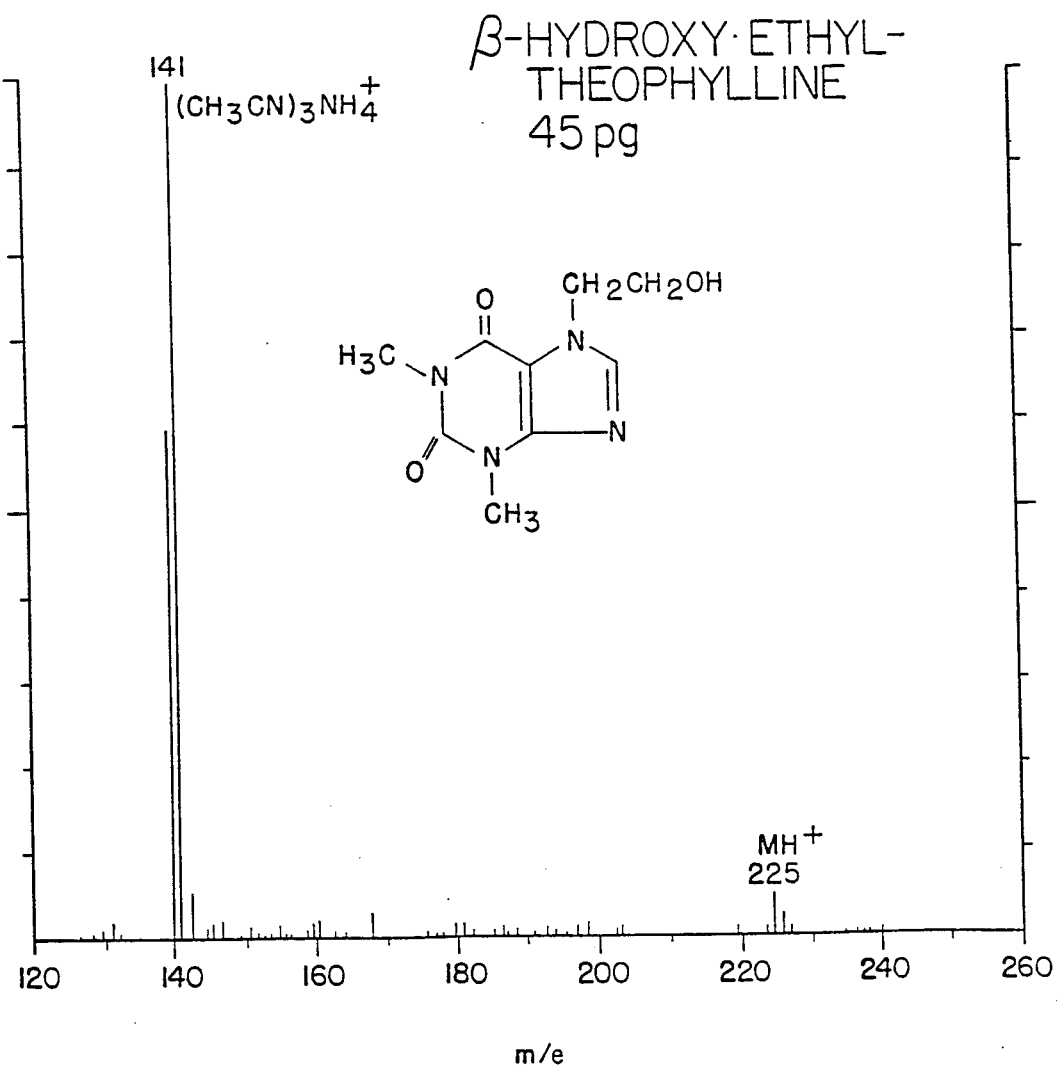
FIG. 7 is a mass spectrum of $\beta$-Hydroxyethyl-Theophylline at trace levels.

A typical spectrum for one of these test compounds at trace levels is shown in FIG. 7. FIG. 7 illustrates mass spectrum obtained from 45 pg of β-hydroxyethyltheophylline injected on column. The chromatographic conditions are the same as for FIG. 6. Peaks other than the MH+ ion at m/e 225 are due to the solvent. In this example, the MH+ ion intensity produced by an injection of 45 pg is the largest peak above m/e 141.

The present invention provides the method and apparatus for controlled vaporization of solutions containing nonvolatile molecules and ions in a manner which avoids salting out, pyrolysis, decompositions, and other uncontrolled chemical modification of the solvated species. The technique is suitable for use in conjuction with liquid chromatography and other methods in which the sample to be analyzed is present in liquid solution and may be used to couple such techniques to gas phase analytical methods such as mass spectrometry and various gas chromatographic detectors including photoionization, electron capture, and flame ionization. It may also be used to remove the solvent in the process of transferring the sample to a surface so that subsequent analyses can be carried out in the absence of solvent interferences and other matrix effects.

Figure 8:
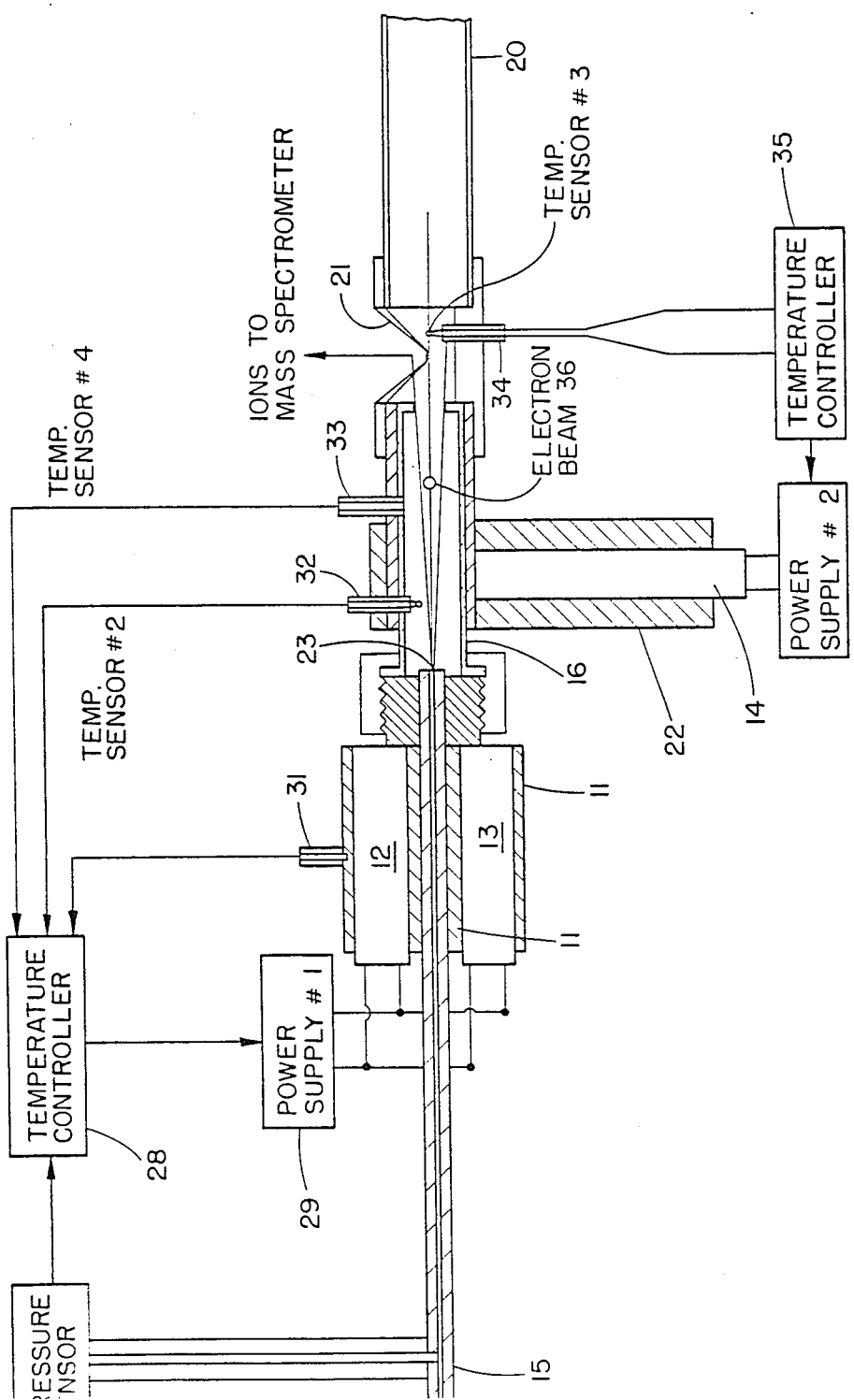
FIG. 8 is a diagrammatic and partially cross sectional view of a second embodiment of the invention.
Figure 11:
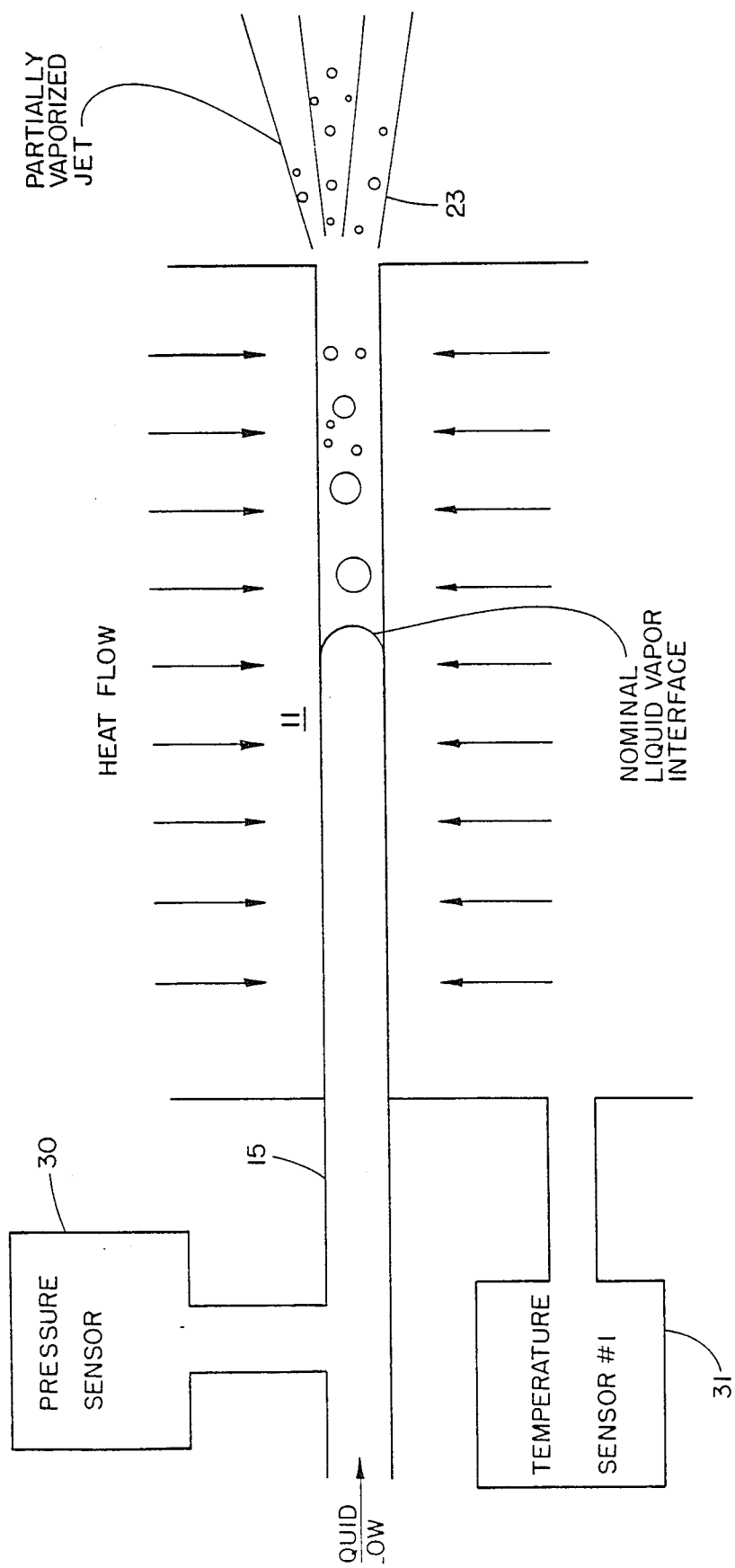
FIG. 11 is a diagrammatic view of an enlarged portion of the apparatus illustrated in FIG. 8.

Diagrams of a second embodiment of the thermospray vaporizer are shown in FIGS. 8 and 11. The liquid sample enters through a capillary tube 15, one end of which is maintained in good thermal contact with a source of heat. Enough heat is supplied to vaporize a sufficient portion of the liquid that the jet 23 emerging from the capillary achieves sonic velocity at the exit. For a given flow rate of a particular solvent the capillary diameter and heated length and heat input must be chosen to achieve this condition. Once proper conditions have been established, stable operation of the vaporizer may be obtained by regulating at 28 the power input to the heater at 29 so as to maintain the temperature pressure measured by one of the sensors 30-34 shown in FIGS. 8 and 11 at a constant value. If the composition and flow rate of the liquid input is maintained constant, then this may be accomplished by merely running at constant power input or by regulating at 28 the power input at 29 so as to maintain the temperature recorded by temperature sensor 31 on the heater block at a constant value. However, if the flow rate or composition of the solvent changes significantly, this method is not effective. For example, if the flow rate or heat vaporization of the solvent decreases and the power input at 29 is maintained constant, the temperature of the vapor emerging from the vaporizer will increase. This can be sensed by thermocouple 33 or other suitable temperature sensor placed in the vapor jet. This sensor could in principle be placed quite close to the vaporizer exit, but equally valid results can be obtained by placing the sensor downstream of the Mach disc and slightly displaced from the axis so as not to unduly perturb the supersonic flow. If the power is controlled at 28 so as to maintain the temperature recorded by sensor 33 at a constant value, then stable operation can be maintained over a significant range of flow and/or heat capacity.

In many cases, the flow is maintained at a constant value by the pump providing the liquid flow, but the composition of the liquid is varied, for example, in gradient elution liquid chromatography. Regulations from temperature sensor 33 can maintain proper operating conditions in this case, correcting the power input at 29 as required by solvent composition changes can also be accomplished by sensing the pressure of liquid stream at a convenient point upstream of the vaporizer as shown at 30 in FIG. 8. Regulating the power input at 28 to the vaporizer so as to maintain this pressure at a constant value provides an alternative method for coping with solvent composition changes.

Figure 9:
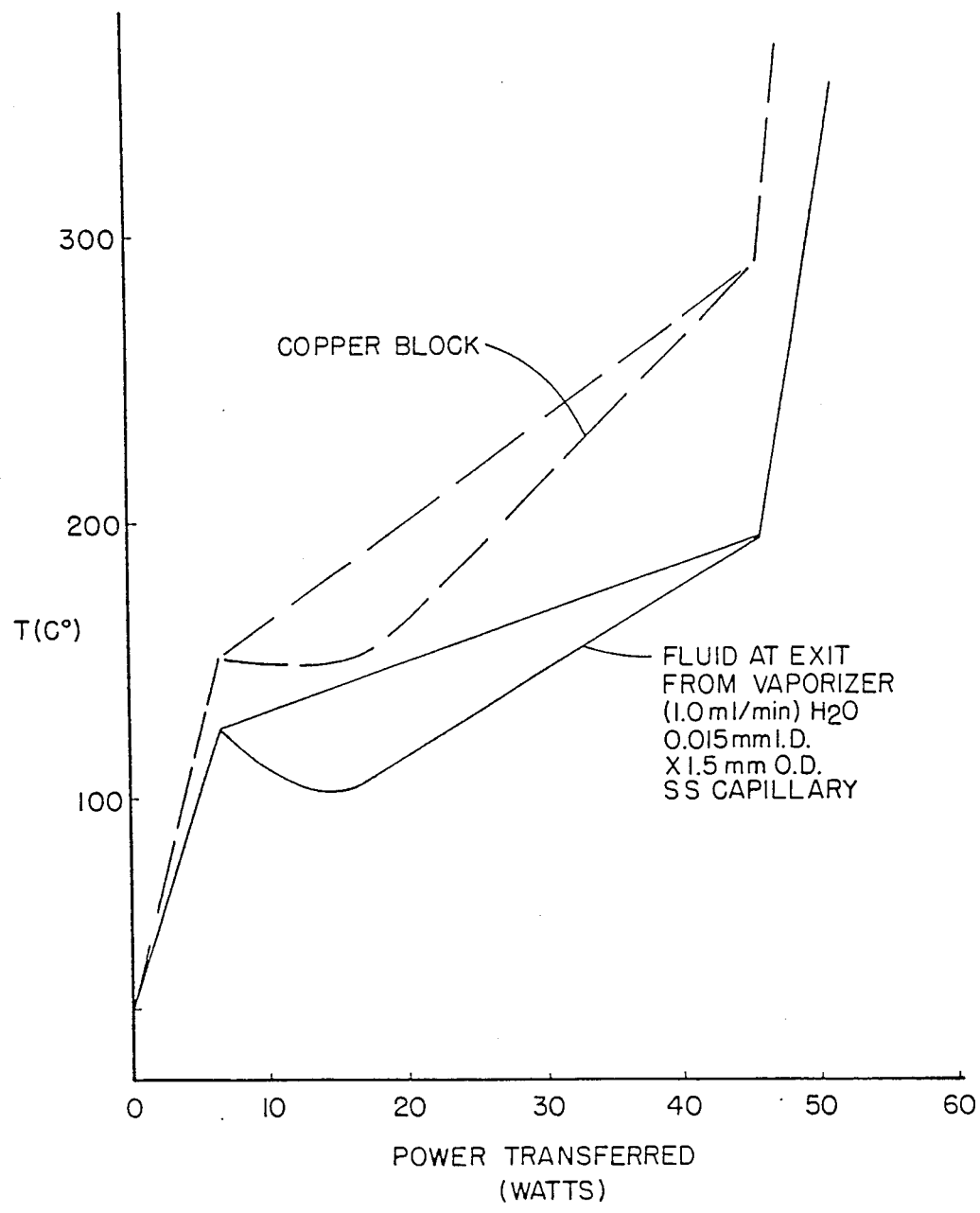
FIG. 9 is a graph of calculated vapor temperatures as a function of input power to the vaporizer heater at a given flow rate of water through a given orifice diameter.
Figure 10:
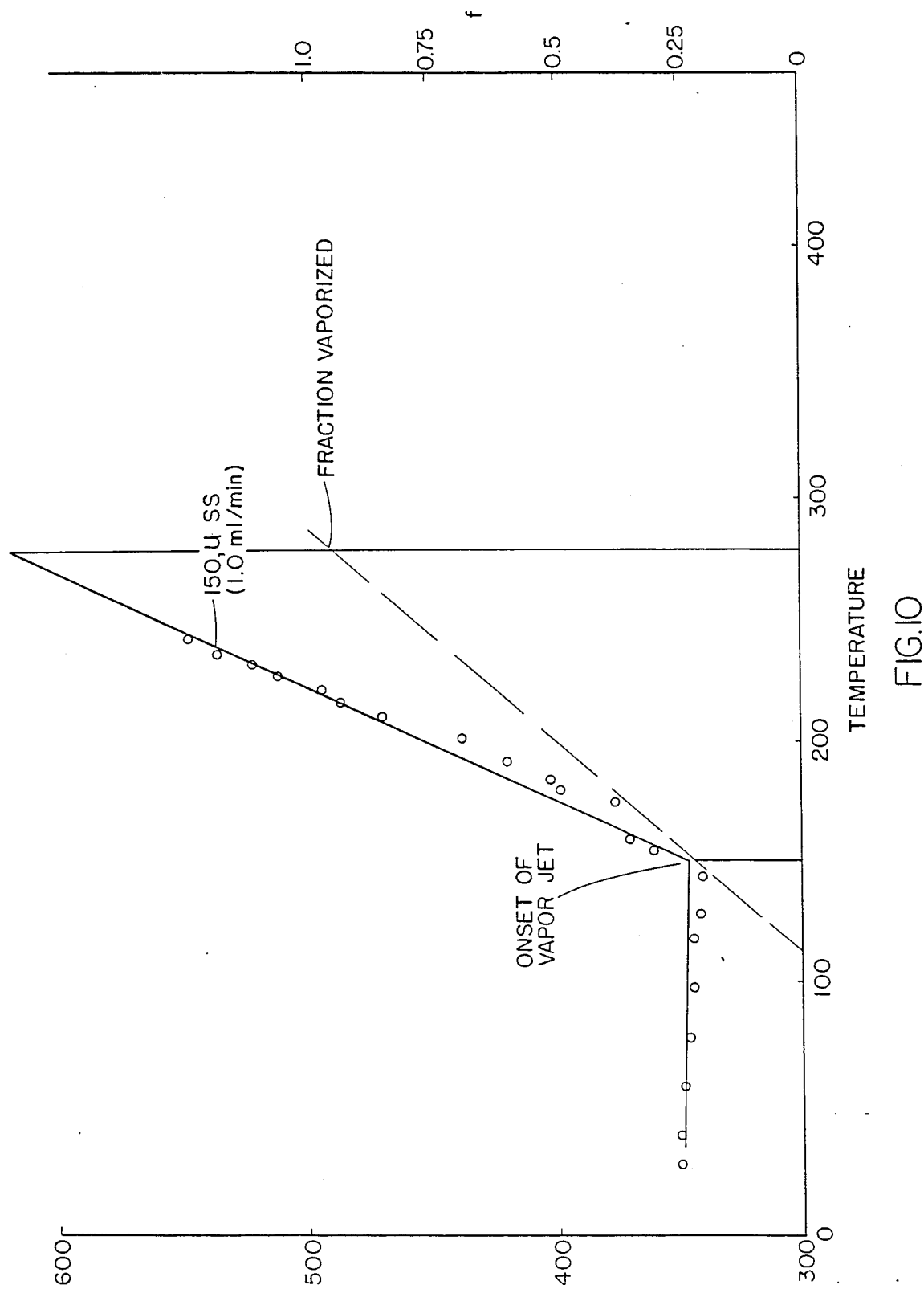
FIG. 10 is a graph of calculated pressure of the liquid stream as a function of pressure and temperature at a given flow rate through a given orifice diameter.

The measured temperature of the vaporizer heating block as a function of power transferred is shown as the upper curve in FIG. 9. The temperature of the fluid at the exit from the vaporizer calculated by subtracting the temperature drop in the heater block and capillary is shown as the lower curve in FIG. 9. The measured pressure of the liquid stream as a function of vaporizer temperature is shown in FIG. 10 together with an estimate of the fraction vaporized as a function of vaporizer temperature. The upward break in the pressure, as shown in FIG. 10, corresponds to the onset of vapor jet formation, and the upward break in the plot of vaporizer temperature as a function of applied power, shown in FIG. 9, corresponds to the point at which complete vaporization of the liquid occurs. These results were obtained with a flow rate of 1.0 mL/min of water through a capillary tube of nominal inside diameter of 0.015 cm. It is essential for most applications of thermospray that complete vaporization not occur within the vaporizer. This is true both for field assisted vaporization of ions and for transfer of nonvolatile samples to surfaces with efficient solvent removal. Since nonvolatile materials tend to be concentrated in the last of the remaining liquid, this also prevents thermal degradation of the nonvolatile solutes.

For applications requiring complete vaporization it is necessary to heat the vapor jet after it exits from the vaporizer. This requires that the jet not be allowed to expand freely into a vacumm, but rather it must be confined so that the adiabatic expansion does not proceed indefinitely. Confinment of the jet may be necessary for almost all applications since otherwise the temperature can become extremely low causing recondensation and other undesirable effects. Heat may be added to the expanding jet using an arrangement such as that shown in FIG. 8. This represents a schematic diagram of the thermospray device as employed for on-line LC-MS both with Chemical Ionization and for direct evaporation of ions from solution. In this case, temperature sensor 34 located just downstream of the ion sampling aperture is used to control at 35 the heat input to the secondary heater 14. The heated region is terminated by an aperture whose size is chosen so as to limit the flow out of the heated region and to introduce some turbulence so that the efficiency of the convective coupling between the walls and the flowing jet is improved.

Similar apparatus may also be used for applications requiring transfer of samples to solid surfaces but the location of the pumping orifice will be different and the operating temperatures required will normally be substantially lower. In some cases, it may be necessary to cool the jet in the secondary region rather than to heat it.

Figure 12:
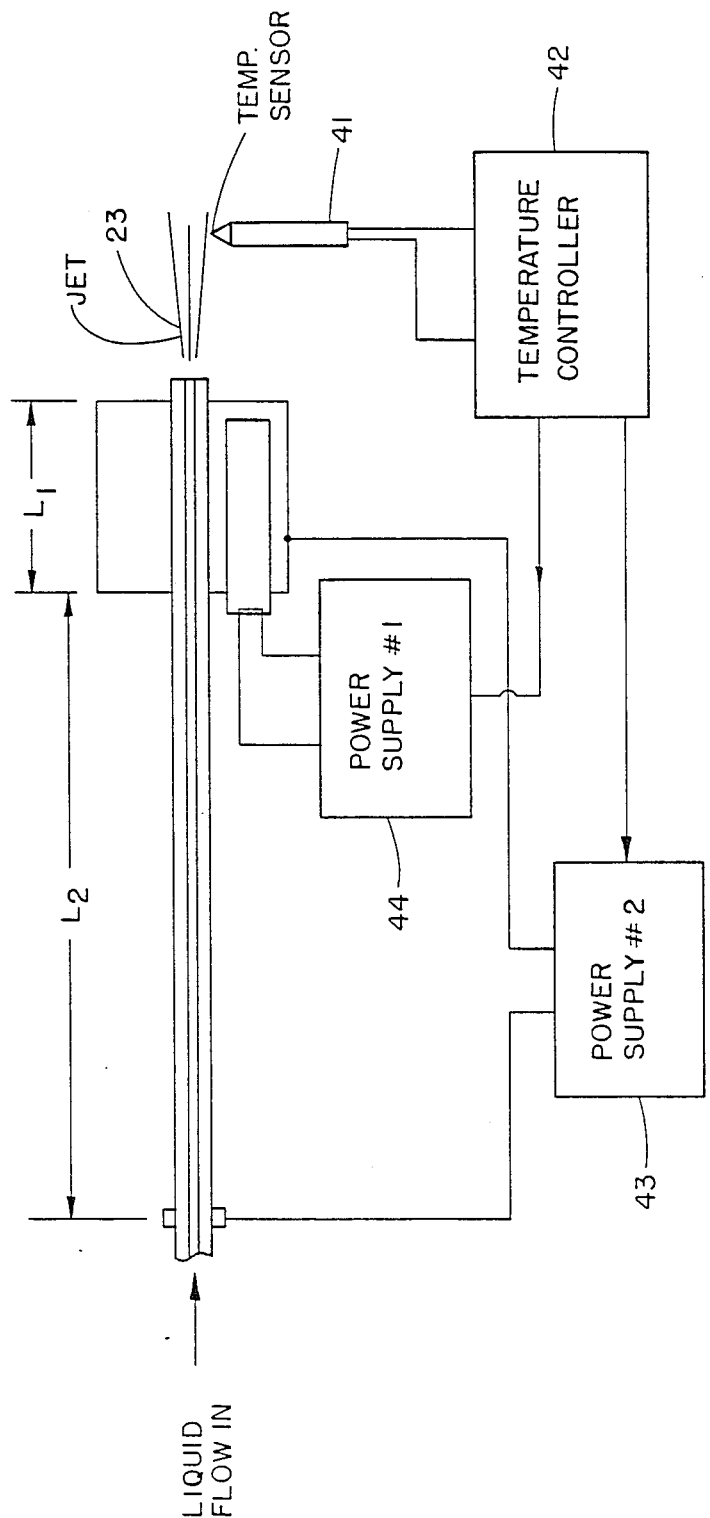
FIG. 12 is a schematic and diagrammatic view of a third embodiment of a thermospray vaporizer using both direct and indirect heating of the capillary.
Figure 20:
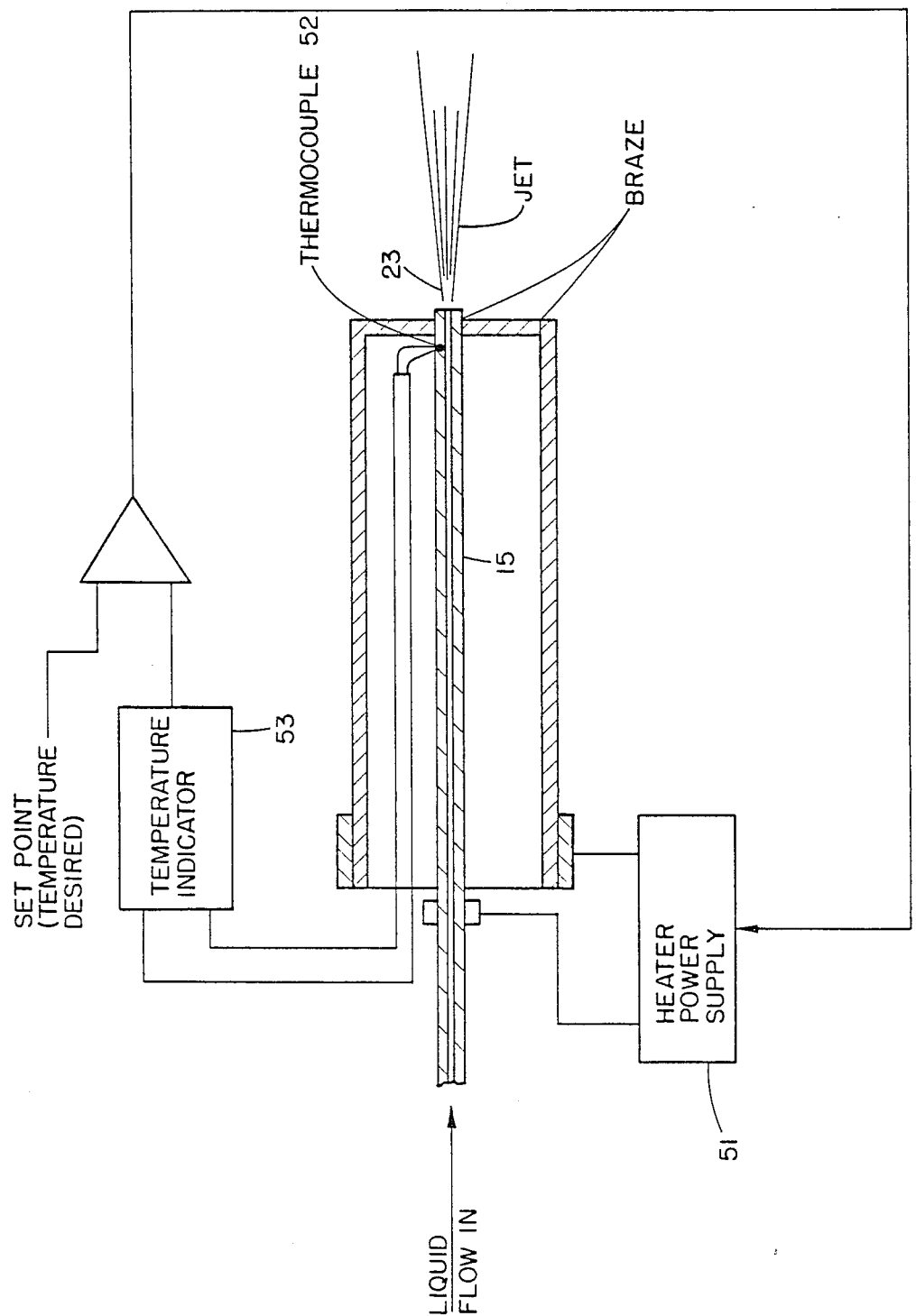
FIG. 20 is a diagrammatic and partially cross sectional view of a fourth embodiment of a thermospray vaporizer using direct Joule heating of the capillary tube.

FIGS. 12 and 20 describe a third embodiment of the invention having two different types of heating sources and a control system needed to maintain a desired degree of partial vaporization even though the solvent composition and flow rate may vary in either a controlled or an uncontrolled manner.

Two alternative ways of supplying the necessary heat to the flowing liquid have been developed. One of these employs commercial cartridge heaters embedded in a block of material with high thermal conductivity (copper) which is in intimate thermal contact with the tube at or near its end. Such thermal contact can be achieved, for example, by silver brazing the end of the tube of the copper block. The other method employs direct ohmic heating of the tube by passing an electrical current through the end portion. The former method has the advantage of providing a very stable input of large amounts of heat without introducing any uncontrolled regions of high temperature in contact with the fluid. The disadvantage of this method is that the thermal mass may make its time response too slow to cope properly with rapid flow changes which sometimes occur. The latter method provides a very rapid and efficient method for coupling heat into the flowing liquid. The disadvantage is that the local temperature depends very strongly on the contact with the liquid, and when operated at high degrees of partial vaporization thermal contact with the fluid becomes poor at the end. As a result the temperature at the end may become so high that the "Leidenfrost" phenomenon effectively prevents further contact in this region and runaway excursion of the temperature near the end of the tube can occur.

Either of these techniques can provide satisfactory performance for some applications, and if the flow rate and composition of the liquid is essentially constant, satisfactory performance can be achieved merely by controlling the power input at the proper level to produce the desired degree of vaporization. This may be accomplished by sensing the heater power directly or by sensing the temperature of the copper block or the tube itself and controlling the heater input so as to maintain this temperature constant.

One of the embodiments that has been found to be particularly useful consists of a combination of these two techniques together with sensing the downstream temperature of the jet. This approach is shown schematically in FIG. 12. The power input is controlled to maintain the temperature constant at the downstream temperature sensor 41, using a standard proportioning controller 42. The proportioning of the heater power between the two heaters 43, 44, can be adjusted manually depending on the application and the characteristics of the flow system. For example, with input from a liquid chromatograph we may have a slowly varying change in solvent composition corresponding to use of gradient elution superimposed on a more rapid, but smaller, fluctuation in flow due to imperfections in the LC pump. In this case a small fraction of the total power (ca. 10-20%) is coupled to the fast response direct heater power supply 43 and the remainder to the slower responding, more stable block heater power supply 44. Both power supplies can be controlled from a single controller since the response of the thermocouple in the jet is fast compared to the thermal response of either heater. The location of the probe in the jet 23 is not particularly critical since the absolute temperature indicated can be correlated with the desired degree of partial vaporization in separate calibration measurements. To avoid disruption of the free jet expansion it is required that this probe be located off the jet axis and downstream of the Mach disk. Controlling the vaporizer heaters and hence degree of vaporization in this manner is a recent innovation, and it appears to have not been used previously, as far as we are aware.

The other recent advance is that we are now able to specify in some detail the geometry of the capillary tube or vaporizer nozzle and the vaporizer heater dimensions which will be most effective for a given range of flow rates and solvent compositions. These designs, which are based primarily on our recent experimental observations, can be rationalized by the following approximate theoretical considerations.

Theoretical Considerations Applicable To These Embodiments

To a good approximation the rate of vaporization of a liquid at temperature T is given by $$Z = \frac{P_v(T) - P_a}{(2\pi mkT)^{\frac{1}{2}}} \qquad (1)$$

where $P_v(T)$ is the equilibrium vapor pressure at temperature T, $P_a$ is the ambient pressure of the vapor, m is the molecular mass, and k is Boltzmann's constant. This expression gives the net flux (no./cm² sec) evaporating. It can be transformed into an effective vaporization velocity by multiplying by the molecular mass and dividing by the density of the liquid to give $$v_v = \frac{(P_v(T) - P_a)}{\rho_L^o} \left(\frac{m}{2\pi kT}\right)^{\frac{1}{2}} \qquad (2)$$

If the liquid is completely vaporized, then the vaporization velocity must be at least equal to the liquid flow velocity which is given by $$v_L^o = Q/A \qquad (3)$$

where Q is the volume flow (cm³/sec) and A is the cross sectional area of the flow channel in the capillary tube. For complete vaporization, conservation of mass requires that $$\rho_L^o v_L^o = \rho_e v_e \qquad (4)$$

where $\rho_e$ and $v_e$ are the density and velocity of the vapor at the exit from the capillary, and $\rho_L$ and $v_L$ are the density and velocity, respectively, of the liquid before it reaches the vaporizer. The maximum velocity with which the vapor can exit the tube is that of the local velocity of sound in the vapor given by $$v_s = (\gamma kT/m)^{\frac{1}{2}} \qquad (5)$$

where $=C_p/C_v$ is the specific heat ratio for the vapor.

Combining equations (4) and (5) and assuming the vapor behaves according to the ideal gas law, we can solve for the pressure of the vapor at the exit from the capillary. The result is given by $$P_e = v_L^o \rho_L^o \, v_s/\gamma \qquad (6)$$

Substituting the exit pressure for $P_a$ in equation (2) and solving for the liquid velocity gives $$v_L = \frac{P_v(T)}{\rho_L^o \, v_s(T)} \left(\frac{\gamma}{\sqrt{2\pi\gamma} + 1}\right) \qquad (7)$$

The temperature at which this equation is satisfied corresponds to the minimum temperature of the fluid at which complete vaporization occurs. This equation can be inverted (at least numerically) to give the minimum temperature for complete vaporization as function of liquid flow. Results for several common solvents are summarized in FIGS. 13 and 14.

Figure 13:
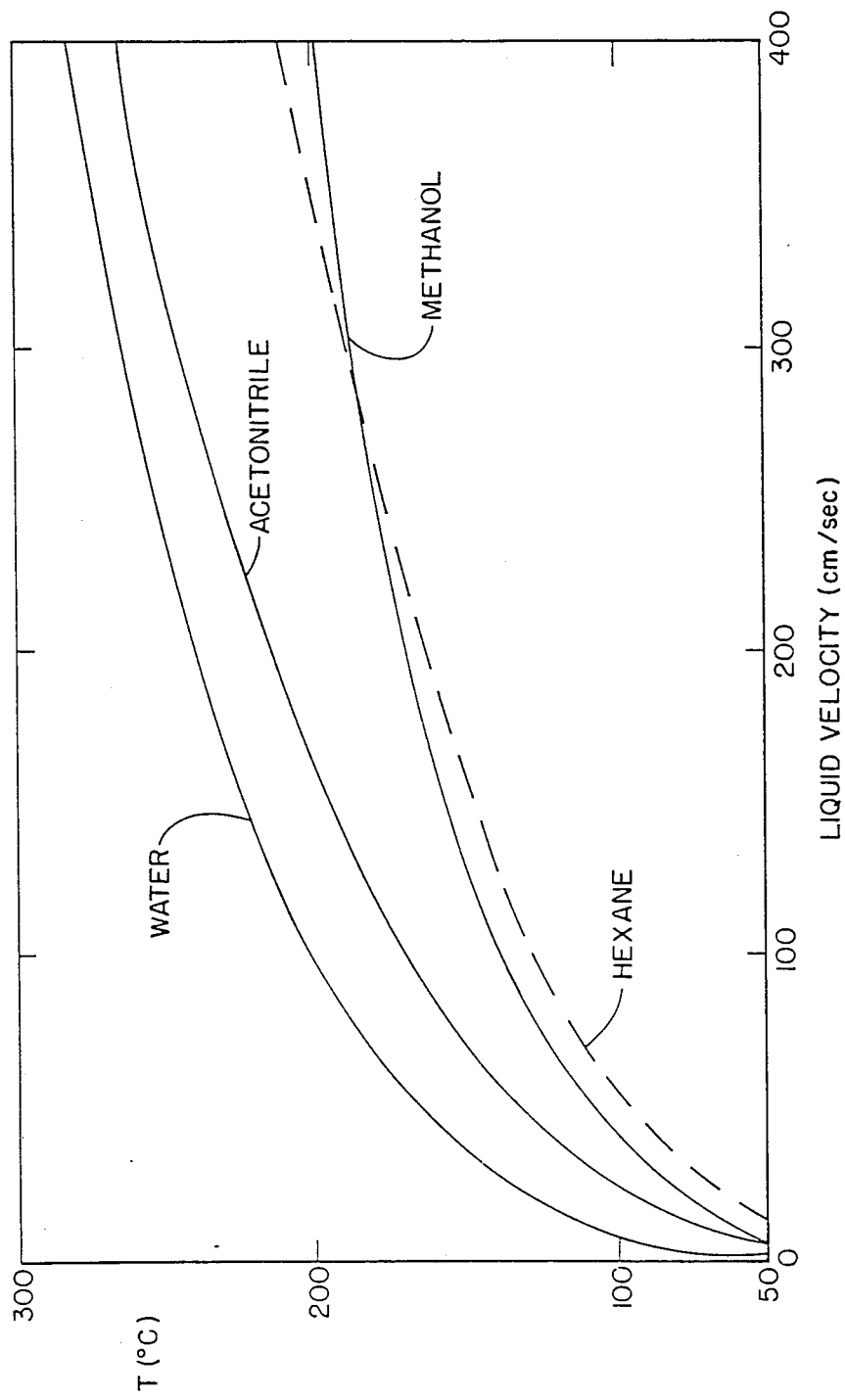
FIG. 13 is a linear plot of minimum vapor temperature for complete vaporization as a function of liquid velocity for several common solvents.
Figure 14:
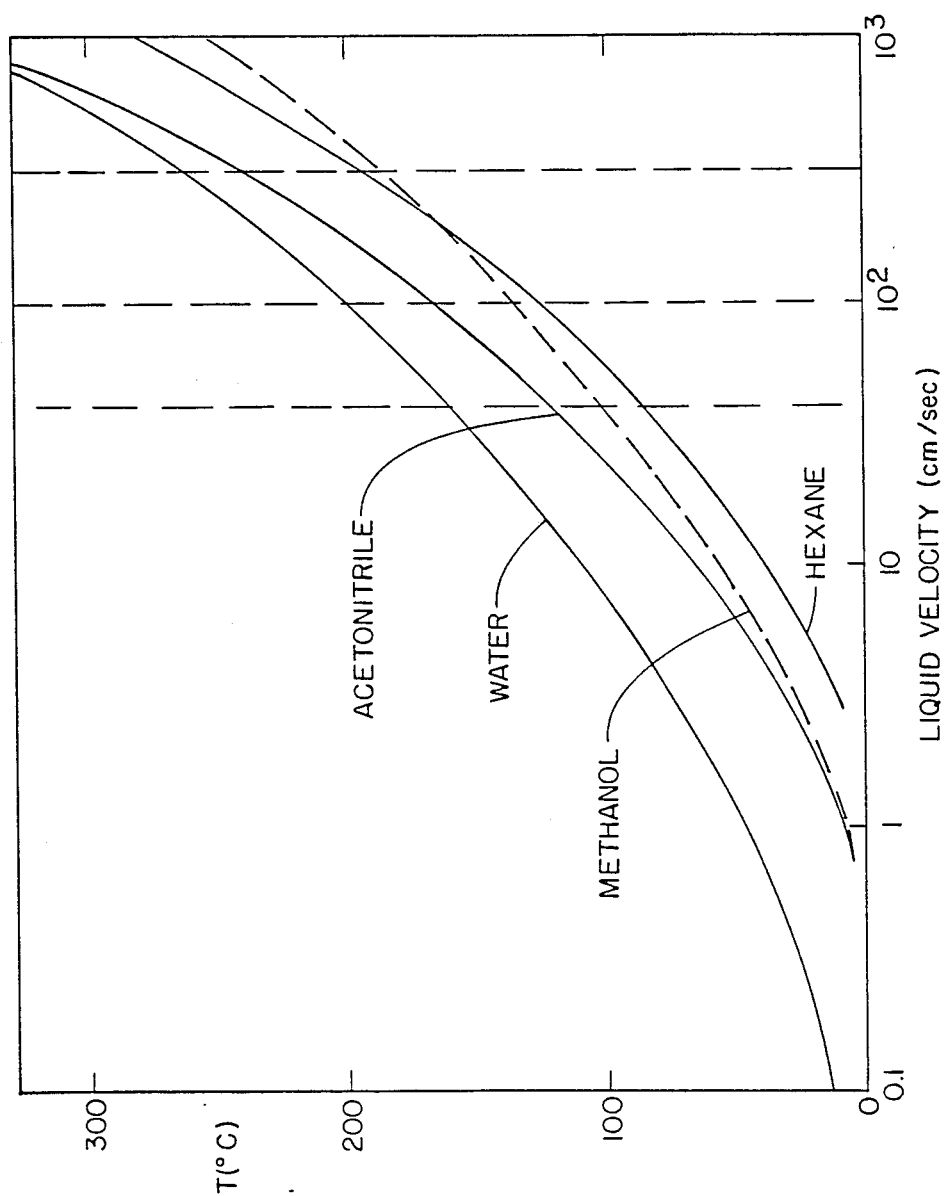
FIG. 14 is a semi-log plot of minimum vapor temperature for complete vaporization as a function of liquid velocity for several common solvents.
Figure 15:
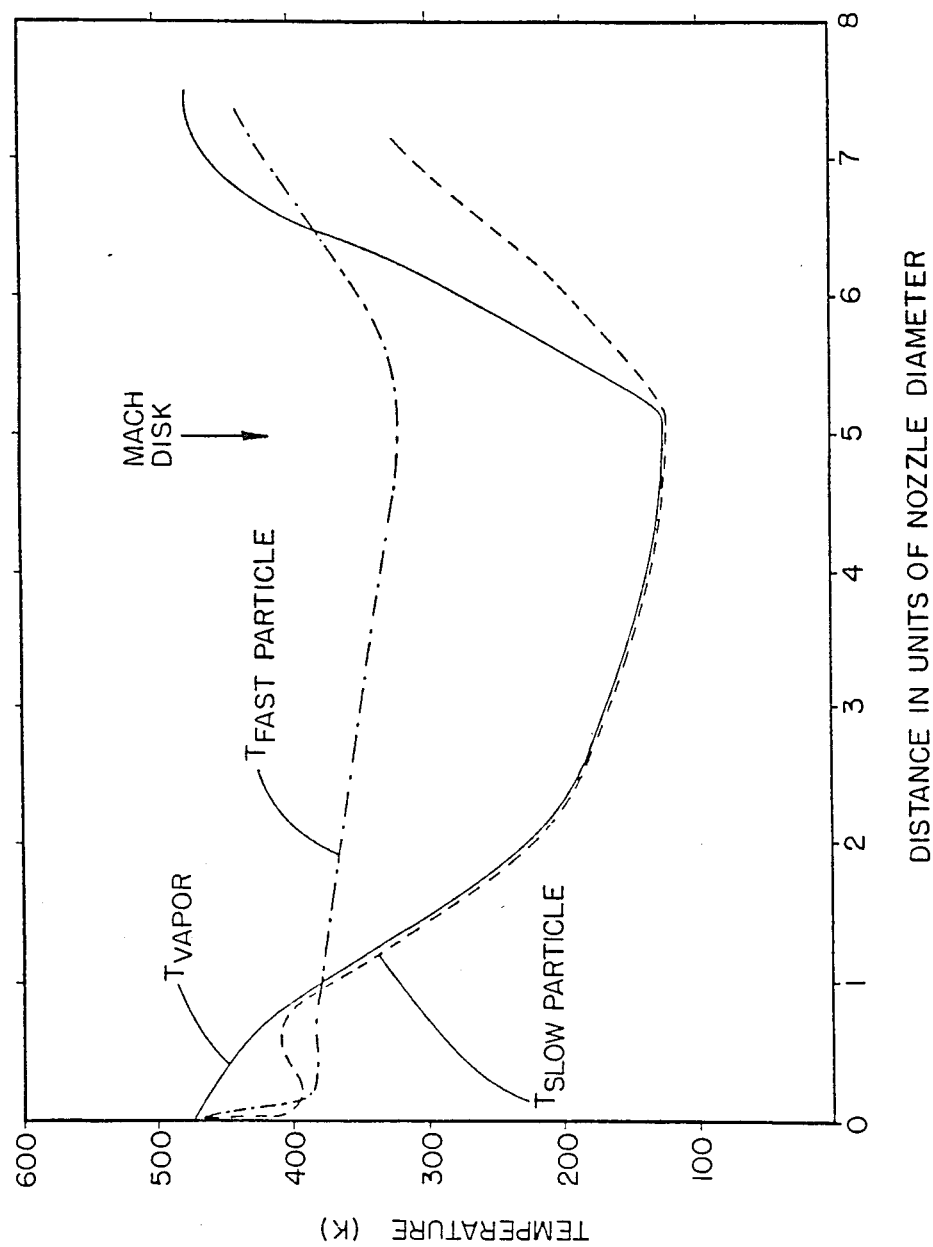
FIG. 15 is a plot of absolute temperature as a function of distance downstream from the vaporizer for vapor and for fast and slow particles or droplet.
Figure 16:
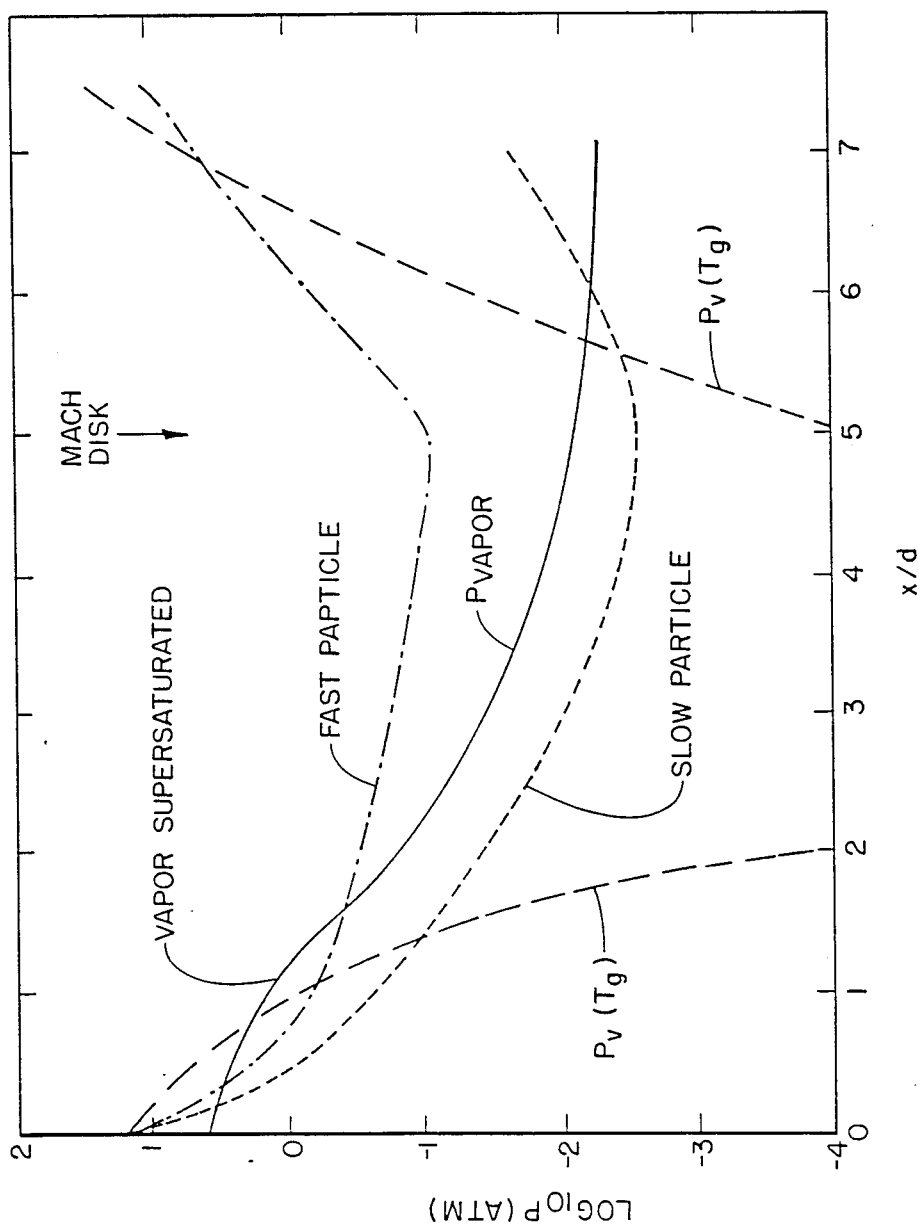
FIG. 16 is a plot of pressure of vapor and vapor pressure of fast and slow particles as functions of distance from the vaporizer.
Figure 17:
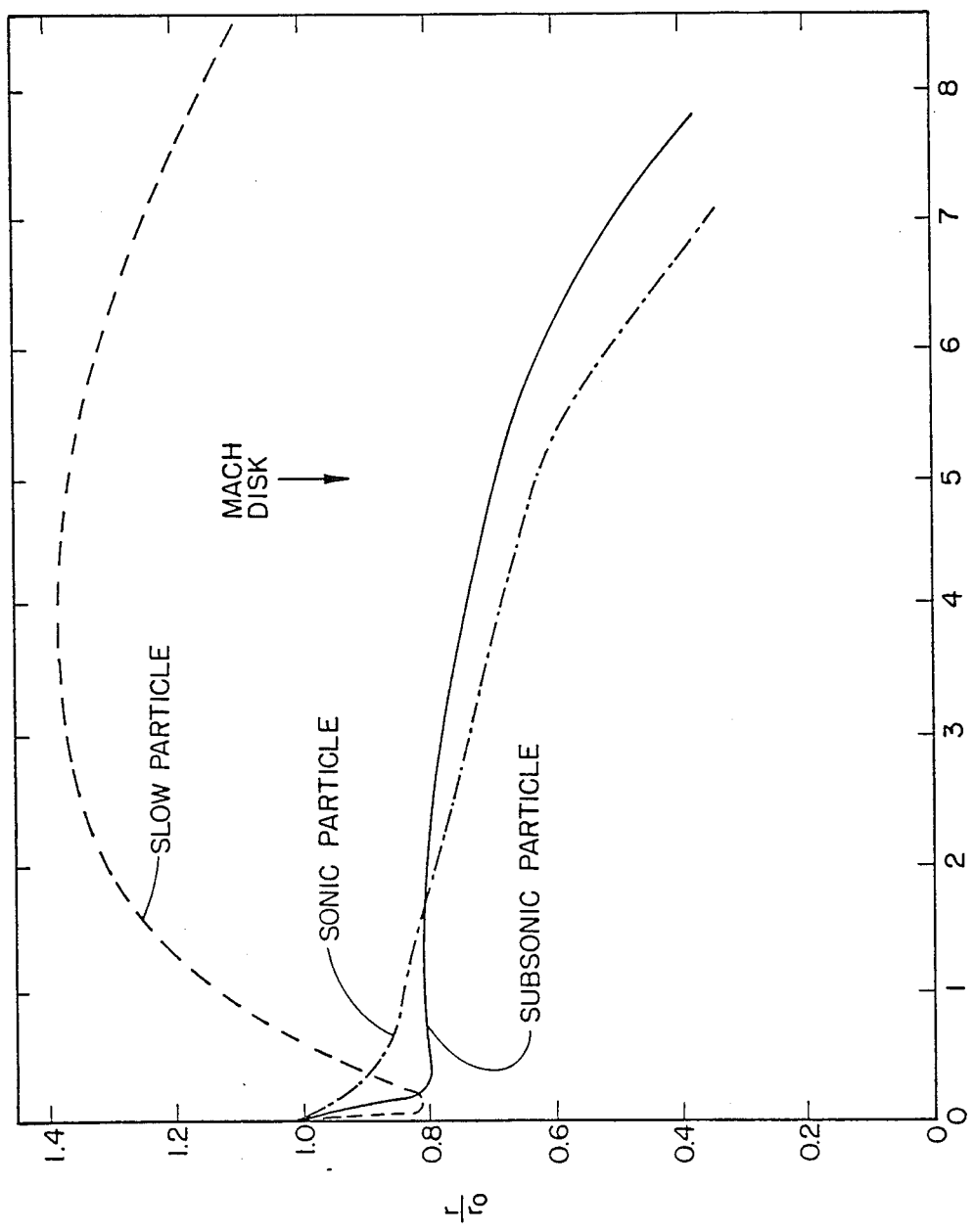
FIG. 17 is a plot of droplet diameter as a function of distance downstream from the vaporizer for different velocity particles.
Figure 18:
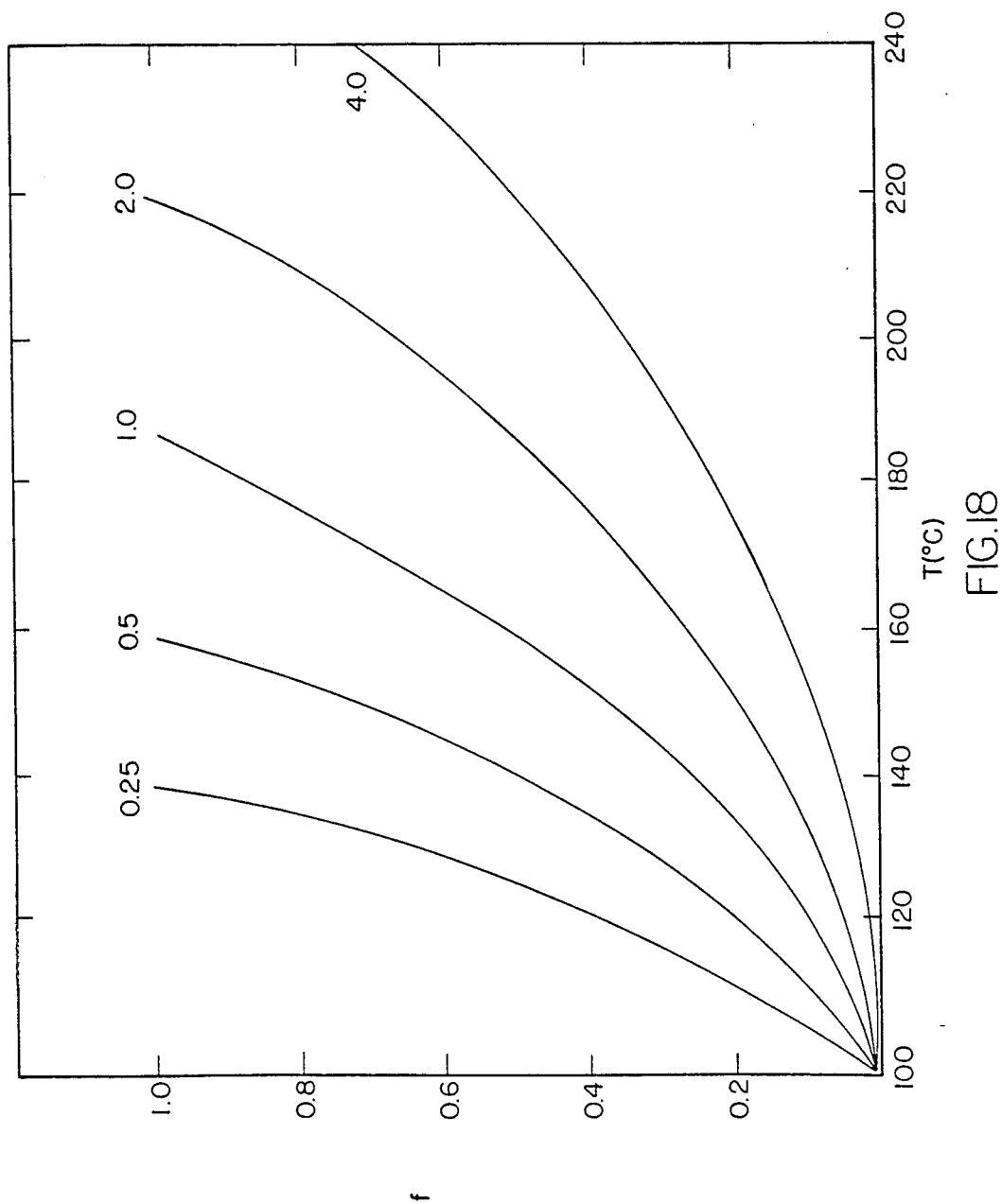
FIG. 18 is a plot of the fraction of water vaporized as a function of exit temperature at an ambient pressure of 1 atom.
Figure 19:
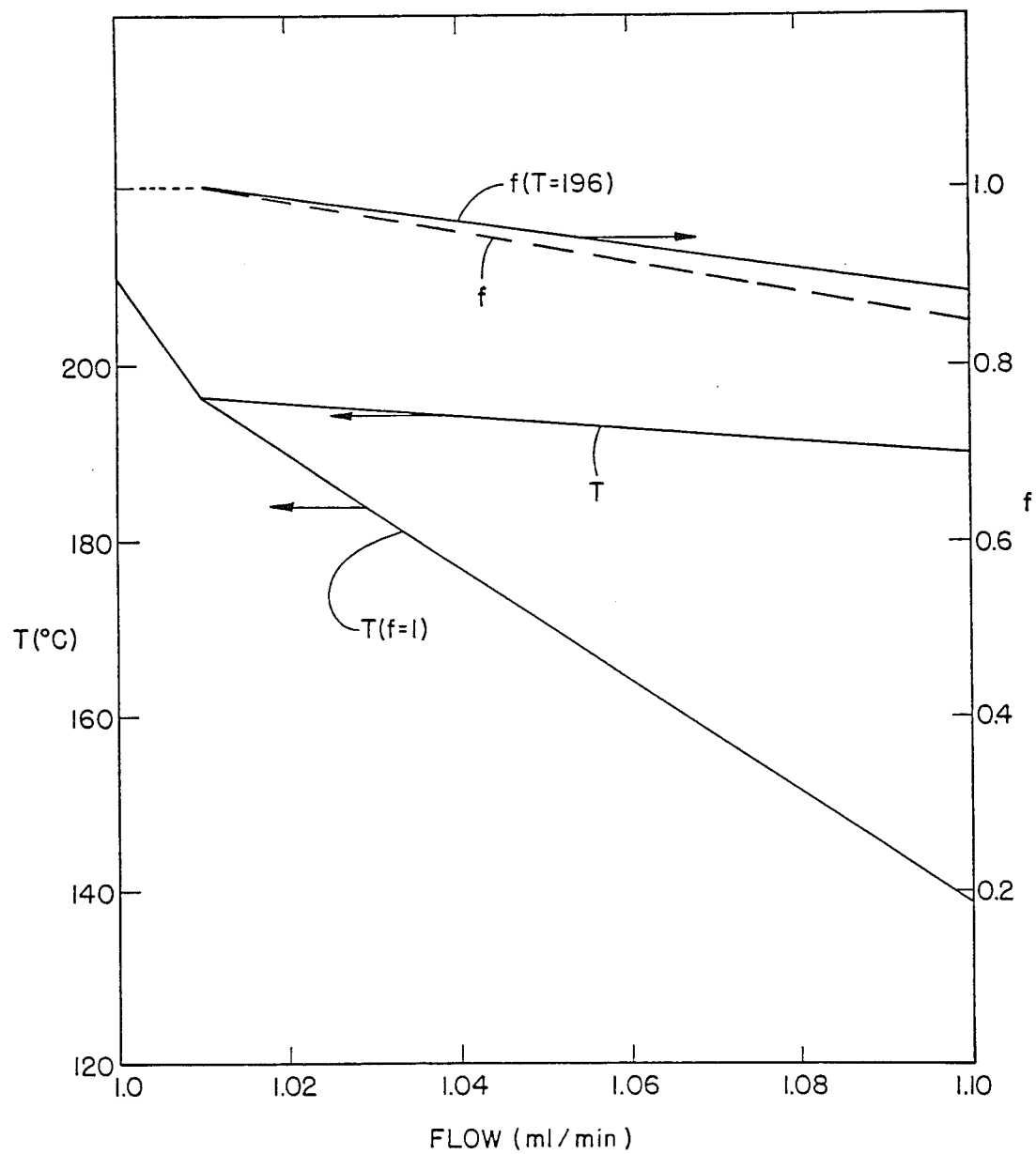
FIG. 19 is a plot of the temperature of exiting fluid and fraction vaporized as functions of flow rate at a constant heating point.

FIG. 13 depicts in a linear plot, the minimum vapor temperature for complete vaporization as a function of liquid velocity for water, acetonitrile, methonol and hexane. FIG. 14 depicts in a semi-log plot, the minimum vapor temperature for complete vaporization as a function of liquid velocity for the same solvents. The central dashed line corresponds to a typical operating point of ca. 1 mL/min through a 0.015 cm ID capillary and the outer dashed lines correspond to approximate outer limits on the operation of this capillary. If the heat supplied to the liquid is more than required to reach these temperatures (for a given flow rate) vaporization will occur prematurely and superheated, dry vapor will emerge from the capillary. If the heat supplied is slightly less than the critical value, then a portion of the liquid is not vaporized and will emerge along with the vapor jet as small entrained droplets. For most applications of thermospray it appears that the best operating point corresponds to a fluid temperature at which partial but nearly complete vaporization occurs. In this range the residual droplets tend to be relatively small and are accelerated to high velocities by the expanding vapor. Since the vapor pressure is a very steep function of the temperature, it is essential to have very precise control of the temperature if a stable fraction vaporized is to be maintained at nearly complete vaporization.

The importance of having the droplets exit with high velocity can be seen by considering the effects of the rapid adiabatic expansion that occurs after the vapor and its entrained droplets exit from the vaporizer. For a free jet expansion of a vapor having sonic velocity at the nozzle exit, the Mach number downstream according to the work of Ashkenas and Sherman is given by $$M = A\left(\frac{x - x_o}{d}\right)^{\gamma-1} - \frac{1}{2A}\left(\frac{\gamma + 1}{\gamma - 1}\right)\left(\frac{d}{x - x_o}\right)^{\gamma-1} \qquad (8)$$

where A=3.82, $x_o$=0.6d, and d is the nozzle diameter. The Mach number is defined as the ratio of the axial velocity $u_g$ to the local speed of sound given by equation (5). For an adiabatic expansion we have $$C_p T_o = (\tfrac{1}{2}) m u_g^2 + C_p T \qquad (9)$$

which can be inverted to give the temperature downstream as $$T = T_o\left(1 + \frac{(\gamma - 1)}{2\gamma} M^2\right)^{-1} \qquad (10)$$

and $$P = P_0^{\gamma/\gamma - 1} \qquad (11)$$

where $T_o$ and $P_o$ are the temperature and pressure, respectively, of the vapor at the exit. The adiabatic expansion continues until the pressure in the jet is comparable to the pressure of the background gas. This is the location of the Mach disc relative to the nozzle. Beyond this point heat transfer between the jet and the background gas becomes important and the jet undergoes a normal shock with the velocities rapidly relaxed back to the local thermal velocity.

During the free jet expansion the entrained liquid droplets become highly superheated (relative to the surrounding vapor) and undergo adiabatic vaporization in which the heat of vaporization for the vaporized portion is supplied by their internal enthalpy. The rate of vaporization of a spherical droplet is given by $$dr/dt = v_v(T) \tag{12}$$

where the vaporization velocity $v_v(T)$ is given by equation (2). Since the process is adiabatic we have $$dH = (-\Delta H_v \rho) dV + C_L \rho V dT = 0 \tag{13}$$

Combining equations (12) and (13) gives $$dT = \frac{\Delta H_v}{C_L} \frac{dr}{r} \tag{14}$$

which can be intergrated to give $$T_o - T = (\Delta H_v/C_L) \ln(r_o/r) \tag{15}$$

If the droplet moves with a velocity $v_p$ then equations (13) and (15) can be combined and intergrated to give an explicit expression relating the distance x that the particle travels and its temperature. This expression is given by $$X = \frac{v_p r_o C_L}{\Delta H_v} \int_{T_o}^{T} \frac{e^{-\left(\frac{C_L}{\Delta H_v}(T_o - T)\right)}}{v_v(T)} dt \tag{16}$$

where variation in the particle velocity with distance has been neglected.

Rapid vaporization of the superheated droplets exiting the vaporizer capillary causes the temperature of the droplets to initially fall more rapidly than the temperature of the vapor in the supersonic jet. Within a short distance downstream (about one nozzle diameter or less) conditions are such that recondensation on the droplets may occur. Fast particles cross through this region sufficiently quickly that very little growth occurs, and throughout the remainder of the free jet expansion the temperature of these particles is above that of the vapor, and the vapor pressure of the particles is above the pressure of the vapor in the surrounding jet. Thus the fast particles will continue to vaporize throughout the free jet expansion, although slowly because the temperature has been reduced by adiabatic vaporization. Slow particles, on the other hand, will tend to approach equilibrium with the vapor in the jet. In this case, after the initial vaporization, the temperature of the slow particles will follow closely that of the vapor. Particle and vapor temperatures as a function of distance from the nozzle are sketched in FIG. 15. FIG. 15 depicts absolute temperature as a function of distance in units of nozzle diameter downstream from the vaporizer for vapor and for fast and slow particles or droplets. If the environment surrounding the free jet is heated, then downstream of the Mach disk heat transfer from the surrounding medium becomes effective and the temperatures of the vapor and particles rises. In this region the particle temperature will lag behind the vapor temperature, with the lag being largest for the slower and larger particles.

The pressure of the vapor in the supersonic jet is sketched in FIG. 16 along with the saturation vapor pressure and the vapor pressures of fast and slow particles. The variation of particle diameter with distance downstream is depicted in FIG. 17. A particle exiting the nozzle with sonic velocity will be rapidly accelerated to supersonic velocity and otherwise will react only weakly with the vapor. The diameter of these particles will decrease monotonically with distance. High velocity (but subsonic) particles will initially vaporize in a shorter distance, but then may grow slightly as they pass through the supersaturated region. Slow particles will grow throughout the free jet expansion will enter the heated region downstream of the Mach disk, much larger and much colder than the smaller droplets.

The average droplet diameter is closely correlated with the fraction of the liquid vaporized within the thermospray vaporizer. As the fraction vaporized approaches unity the droplet diameter becomes small and the velocity high. As a given flow rate and capillary diameter; the fraction vaporized is given by the ratio of the vaporization velocity, given by equation (2), to the liquid velocity, given by equation (3). The relationship between fraction vaporized and temperature is shown for several flow rates through a 0.15 mm diameter capillary in FIG. 18. These results were calculated for an ambient pressure of 1 atm.

As long as the flow rate is constant, the temperature of the exiting vapor and the fraction can be maintained at a constant value by merely keeping the heater power input to the vaporizer constant. However, the flow rates are frequently subject to small uncontrolled changes due to imperfections in the liquid pumping system. If the fraction vaporized is less than or equal to one, the heat input is related to the exit temperature by an equation of the form $$W=\Delta H_v\rho Qf+C_L\rho Q(T_e-T_o) \quad (17)$$

where is the enthalpy of vaporization per unit mass, $C_L$ the heat capacity of the liquid per unit mass, $\rho$ the liquid density, f the fraction vaporized, and Q the liquid flow rate. $T_e$ is the exit temperature and $T_o$ the ambient temperature of the liquid. Temperature dependence of the enhalpy of vaporization, heat capacity and density are neglected. At constant heat input, W, a change in flow will cause the fraction vaporized and the exit temperature to change as implied by equation (17). If the temperature and fraction vaporized were independent variables then either might change as a function of flow rate (at constant W) as illustrated in FIG. 19. However, these two parameters are related (for given flow rate) as illustrated in FIG. 18, and since the term in equation (17) corresponding in vaporization is large compared to that for heating the liquid, the major effect of changing the flow rate is to change the fraction vaporized accompanied by a smaller change in exit temperature.

This is illustrated in FIG. 19 which depicts the temperature of exiting fluid and fraction vaporized as functions of flow rate at constant heat input rate. (50 watts) Curve T(f=1) corresponds to calculated temperature if fraction vaporized were to remain constant at unity. Curve f(T=196) corresponds to calculated f if T were to remain constant at 196° C. Curves f and T correspond to actual calculated fraction vaporized and exit temperature, respectively.

If vaporizer is operated at nearly complete vaporization, then a drop in flow rate can cause a rapid increase in exit temperature because when complete vaporization has been achieved only the heat capacity of the vapor is available to absorb the excess heat input. Under the conditions illustrated in FIG. 8, a 1% increase in flow above the point at which complete vaporization occurs will cause a drop of about 1.3% in the fraction vaporized and a 0.6° C. drop in exit temperature. On the other hand a 1% decrease in flow from this point will lead to an increase in exit temperature of about 12° C. This latter increase may be somewhat moderated by decreased heat transfer efficiency for the vapor as compared to the liquid. In any case complete vaporization leads to a reduction in thermal dissipation from the exit portion of the vaporizer heater and can lead to thermal runaway if uncontrolled.

Control of the Thermospray Vaporizer

From the above theoretical considerations and recent experimental work it is now possible to rationally design the thermospray vaporizer for any application. The important design parameters for the vaporizer are the following:

(1) The inside diameter of the vaporizer capillary.
(2) The length of heated zone.
(3) The maximum permissible temperature at the inner surface of the capillary.
(4) The thermal time constant of the heater.

In all of the above discussion it is assumed that the liquid channel is of uniform cross section. While it significantly complicates the analysis and makes construction somewhat more difficult, it may be advantageous in some cases to have the cross section smaller near the exit. This would allow higher temperatures and velocities at the exit while allowing lower liquid velocities in the region where the major part of the heat transfer is occurring.

In choosing the optimum values for the above parameters the following information about the operating conditions is needed:

(1) The solvent flow rate and composition.
(2) The degree of vaporization required.
(3) The maximum permissible temperature of the fluid in the vaporizer.
(4) The magnitude and time constants of uncontrolled variations in flow rate or solvent composition.

The other important considerations in designing a thermospray system are the method used for determining the state of the fluid exiting the vaporizer and the way in which this information is used to control the power input to the vaporizer to achieve the desired operating condition. It is clear from the theoretical discussion that the best measure of the performance of the vaporizer is the temperature of the vapor at the exit. This temperature could be sensed by a probe placed directly into the vapor jet at this point, but for most applications this placement of the temperature probe would produce an unacceptable perturbation of the flow. It has been found that an acceptable measure of vaporizer operating point can be obtained from a probe placed downstream of the Mach disk. The temperature of a probe in this location responds closely to variations in temperature at the exit from the vaporizer, but it also depends on the temperature of the environment and the heat input from the downstream heater. It appears that the best location for the controlling temperature sensor is to attach to the capillary tube at or near the exit. In this region the temperature of the tube must be very close to the temperature of the exiting vapor. Furthermore the response of the temperature measurement at this point should track very closely with rapid changes in the vapor temperature.

Another way of monitoring the performance of the vaporizer is the measure the pressure in the liquid upstream of the vaporizer. This pressure corresponds to the pressure drop due to flow of liquid through the tube plus the pressure produced by the vaporization. Variations of pressure with temperature are dominated by the second contribution; and for a given liquid composition and flow velocity it is uniquely related to the exit temperature, for example as implied by equation (7). One of the potential problems with this approach is that the relationship between pressure and temperature may change, for example, due to partial occlusion of the liquid channel. If such an occlusion occurs upstream the pressure would increase due to a change in liquid flow impedance even though the vaporization conditions had not changed, and the pressure indication would not provide the correct input for control of the vaporizer. On the other hand, if partial occlusion occurs at or near the exit of the vaporizer, both the exit temperature and the pressure will rise together at constant power input (and constant fraction vaporized). If the power is adjusted to keep either the exit temperature or upstream pressure constant, the fraction vaporized will decline as the vapor velocity increases due to an occlusion at or near the tip. At constant flow rate and solvent composition this condition can be detected by monitoring the power input to the heater.

The exit temperature, the upstream pressure, and power input are related to the liquid flow velocity and fractional vaporization as discussed above and in the preceding theoretical discussion. The liquid flow rate and solvent composition are nominally controlled by the liquid pumping system. If the liquid flow rate and composition, power input, liquid pressure, and exit temperature are all monitored, then the fractional vaporization is uniquely determined independent of any uncontrolled changes in effective vaporizer diameter which might occur as a result of partial occlusion. Since modern liquid chromatographic pumps are often operated under control of a microprocessor, it appears feasible to select the desired solvent flow rate, composition and fractional vaporization, and to program the microprocessor to automatically adjust conditions so that the fraction vaporization is maintained constant both with changes in solvent composition and flow rate and with uncontrolled changes in vaporizer characteristics which might be introduced by partial occlusion of the flow channel. In the event that such occlusions causes the exit temperature or liquid pressure to exceed preset limits, an alarm showing incipient failure could be triggered.

The range of operating temperatures which are used depends to a great extent on the application and the kinds of samples to be analyzed. For example, it has been found for direct liquid chromatograph to mass spectrometer analysis on nonvolatile compounds, separated by a reversed phase high pressure liquid chromatograph using water-methanol or water-acetonitrile, that vapor temperatures in the range from ca. 150° to 250° C. give good results in most cases. These conditions are compatible with a 0.15 mm capillary and flow rates in the range from 0.5 to 2 ml/min, corresponding to liquid velocities in the range of ca. 50 to 200 cm/sec. At these velocities, a heater length on the order of 3 cm is adequate to provide sufficient heat transfer without exceeding the limitations on surface temperature.

If we wish to adapt this technique to microbore liquid chromatography, where the flow rates may be an order of magnitude or more lower, then to maintain comparable operating conditions the area of the capillary channel must be reduced as the flow rate is reduced in order to maintain a similar range of liquid velocities and corresponding exit temperatures. On the other hand, it is important in many applications that the sample not be significantly vaporized within the vaporizer. In the case of relatively volatile or thermally labile samples, this may limit the maximum permissible temperature in the vaporizer. This implies that the liquid flow velocity must be limited, and given solvent flow rate and composition may dictate an increase in the diameter of the capillary channel.

The ability of the control system to correct for variations in liquid flow or solvent composition depends mainly on the time constant of the temperature sensor and of the vaporizer heater. These time constant are determined by the heat capacities and the rates of energy input and dissipation. To allow correction for rapid changes, for example due to pump imperfections, it is important to keep the masses of the heaters and sensors rather small.

The extent of vaporization which is desirable depends to some extent on the particular application, but it appears that most applications which we have considered so far involve operation at very nearly complete vaporization where both the particle velocities and the temperatures of the droplets and vapor are highest. As the jet undergoes an adiabatic expansion, the temperatures of both the vapor and the droplets decrease rapidly leading eventually to complete quenching of further vaporization. For most applications it appears desirable to limit the duration of the adiabatic expansion so that the temperature in the jet does not get too low. In many cases additional heat is added downstream of the Mach disk to effect further vaporization. Individual cases are discussed below.

If the droplets or particles produced in the thermospray vaporizer are charged sufficiently, then ions as well as neutrals may be vaporized. If the solution being vaporized contains ions in solution, then the droplets are charged by a symmetric charging mechanism. Other charging mechanisms may also be involved, and other methods of adding charge (e.g. electrical discharge) may also be employed. While a completely satisfactory theory of field-assisted vaporization of ions from liquid surfaces is not yet available, it appears that surface field strengths on the order of $10^8$ V/m are required for evaporation rates for ions to be comparable to those for neutrals. It appears that some of the droplets produced when thermospraying aqueous electrolytic solutions (e.g. 0.1M ammonium acetate) may initially be small enough and highly enough charged to emit ions as they exit the vaporizer nozzle. However, due to the rapid cooling that results from evaporation of the droplets during the adiabatic expansion, this ion emission will not persist unless some additional heat is added downstream to assist in further vaporization of both ions and neutrals.

A schematic diagram of the second embodiment which we have found effective for on-line liquid chromatograph mass spectrometry analysis is shown in FIG. 8. In this arrangement temperature sensor 32 is used to control the heat input to the vaporizer as described above, and temperature sensor 34 is used to monitor the temperature of the vapor just downstream of the point at which ions are sampled into the mass spectrometer. In between these two points is an enclosed and heated region which serves to limit the extent of the adiabatic expansion. Once proper operating conditions have been established, the output of temperature sensor 34 can be used to control the heat input in the auxiliary heater 14 so as to maintain this temperature at a constant value.

This apparatus is also useful when ions are not present in solution, but in this case an external source of ionization is required. The electron beam indicated at 36 serves this purpose and is normally used only when insufficient ionization is available in the solution. The use of this external source of ionization allows both positive and negative ion chemical ionization of samples.

From theoretical consideration of the desired characteristics of the thermospray vaporizer, we now feel that the version using only direct Joule heating of the capillary tube may be superior for most applications. This fourth embodiment is illustrated in FIG. 20. This approach allows the thermal mass of the heater to be small compared to that of the flowing liquid, and allows the use of a very short time constant. We had previously rejected this concept because of concern about thermal runaway occurring as a result of overheating near the exit. We now believe that this can be avoided by controlling the heater power 51, from a thermocouple 52 placed in intimate thermal contact with the capillary tube at or very near the exit. This temperature sensor output 53 is connected to an operational amplifier 54 which is controlling the heater power supply 51. A block diagram of this embodiment is shown in FIG. 20. In this case the heater power supply 51 will be either a DC supply or an AC supply operating at a high enough frequency that the period is short compared to the time constant of the heater. This system allows for automatic correction for flow fluctuations produced by imperfections in the pumping system.

We claim:

1. A method of forming an ion vapor from a liquid sample, said liquid sample being passed through a capillary tube of a vaporizer and discharged therefrom as a thermospray of minute particles for analysis of vaporized ions of interest, said method comprising:
    heating the capillary tube along a predetermined length thereof;
    sensing the temperature of the liquid sample at a predetermined location within the vaporizer;
    automatically controlling heating of the capillary tube and thereby the temperature of the liquid sample being passed therethrough in response to the sensed temperature to form a thermospray of vapor and unvaporized minute particles, the thermospray having a constant degree of partial vaporization when discharged from the capillary tube;
    providing a confining chamber downstream from the capillary tube for receiving at least a portion of the thermospray discharged from the capillary tube and for limiting adiabatic expansion of the vapor discharged from the capillary tube; and
    heating the vapor within the confining chamber to vaporize substantially all the discharged minute particles within the confining chamber by contact with the heated vapor; and
    thereafter withdrawing from the confining chamber, for analysis, the vaporized ions of interest.

2. The method of forming an ion vapor as defined in claim 1, wherein the step of sensing the temperature of the liquid sample comprises:

sensing the temperature of the capillary tube adjacent a discharge end of the capillary tube.

3. The method of forming an ion vapor as defined in claim 1, wherein the capillary tube is electrically conductive, and the step of heating the capillary tube comprises:
heating the capillary tube with a two stage heater, the heater having a first stage secured in thermal contract with the capillary tube for applying thermal energy to the first stage and thence to the capillary tube, and having a second stage for applying electrical energy to the electrically conductive capillary tube for direct resistance heating of the capillary tube.

4. The method of forming an ion vapor as defined in claim 1, wherein the step of heating the vapor comprises:
sensing temperature within the confining chamber; and
automatically controlling heating of the vapor within the confining chamber in response to the sensed chamber temperature.

5. The method of forming an ion vapor as defined in claim 1, further comprising:
controlling pressure within the confining chamber by removing vapor from the chamber with a vacuum pump.

6. The method of forming an ion vapor as defined in claim 1, wherein:
said liquid sample includes ions of interest for analysis; and
said liquid sample contains additional ions which are not themselves of interest for analysis but which serve to increase the charge on the minute particles discharged from the capillary tube to increase the efficiency with which ions of interest are vaporized.

7. The method of forming an ion vapor as defined in claim 1, wherein said liquid sample includes molecules of interest, and said method further comprises:
ionizing the molecules of interest within the confining chamber to form vaporized ions of interest for analysis.

8. The method of forming an ion vapor as defined in claim 1, further comprising:
forming said capillary tube with a substantially uniform interior cross-sectional diameter; and
restricting the uniform interior cross-sectional diameter at a nozzle end of capillary tube to increase the temperature of the thermospray discharged from the capillary tube.

9. The method for forming an ion vapor as defined in claim 5, wherein the step of controlling pressure within the confining chamber further comprises:
providing a flow constricting aperture through the confining chamber; and
passing the vapor through the flow constricting aperture and thence from the confining chamber for analysis of the vaporized ions of interest.

10. The method of forming an ion vapor as defined in claim 1, wherein the step of automatically controlling the heating of the capillary tube comprises:
maintaining from 1% to 35% of the sample in liquid form as it is discharged from the capillary tube.

11. A thermospray vaporizer for obtaining an ion vapor from a liquid sample for analysis of vaporized ions of interest, the vaporizer comprising:
a capillary tube means defining a discharge nozzle at an end thereof for passing the liquid sample therethrough;
a temperature sensing means for sensing the temperature of the liquid sample at a predetermined location within the vaporizer;
first heating means for heating a predetermined length of the capillary tube means and thereby heating the liquid sample passing therethrough;
control means for regulating the first heating means in response to the temperature sensing means to partially vaporize the liquid sample within the capillary tube and to form a thermospray of vapor having ions of interest and unvaporized minute particles, the thermospray having a constant proportion of vapor to unvaporized particles when discharged from the capillary tube means;
confining means forming a chamber for receiving at least a portion of the thermospray discharged from the capillary tube means to limit adiabatic expansion of the discharged vapor; and
second heating means for heating the vapor within the confining means to vaporize substantially all the discharged minute particles within the confining means by contact with the heated vapor.

12. The thermospray vaporizer as defined in claim 11, wherein the discharge nozzle of the capillary tube means has a restricted diameter to increase the temperature of the thermospray discharged from the capillary tube means.

13. The thermospray vaporizer as defined in claim 11, further comprising:
a vacuum pump for withdrawing vapor from the confining means for controlling pressure within the chamber.

14. The thermospray vaporizer as defined in claim 11, wherein:
said capillary tube means is electrically conductive; and
said first heating means includes a circuit for applying electrical energy to a predetermined length of said capillary tube means for direct resistance heating thereof.

15. The thermospray vaporizer as defined in claim 11, wherein said second heating means comprises:
a downstream temperature sensor for sensing temperature within the chamber; and
a downstream control means for automatically regulating the second heating means in response to the downstream temperature sensor.

16. The thermospray vaporizer as defined in claim 11, wherein said confining means comprises:
a flow constricting aperture between the chamber and an ion sampling aperture for passing the vaporized ions of interest.

17. The thermospray vaporizer as defined in claim 11, wherein the temperature sensing means senses the temperature of the capillary tube means to obtain a derivative value of temperature of the liquid sample in the capillary tube means.

18. The thermospray vaporizer as defined in claim 11, wherein the first heating means comprises:
a thermoblock in physical engagement with the capillary tube means for applying thermal energy to a predetermined length of the capillary tube means.

19. The thermospray vaporizer as defined in claim 11, wherein:

said liquid sample includes ions of interest for analysis; and said liquid sample contains additional ions which are not themselves of interest for analysis but which serve to increase the charge on the minute particles discharged from the capillary tube to increase the efficiency with which ions of interest are vaporized.

20. The thermospray vaporizer as defined in claim 11, wherein said liquid sample includes molecules of interest, and said vaporizer further comprises:

ionizing means for ionizing the molecules of interest within the chamber.

* * * * *

UNITED STATES PATENT AND TRADEMARK OFFICE
CERTIFICATE OF CORRECTION

PATENT NO. : 4,861,989

DATED : August 29, 1989

INVENTOR(S) : M. L. Vestal, et al.

It is certified that error appears in the above-identified patent and that said Letters Patent is hereby corrected as shown below:

Column 15, line 50: "$P_e = v_L{}^o P_L{}^o v_s / T$" should read as --$P_e = v_L^o \; \rho_L^o \; v_s / \gamma$--

Signed and Sealed this

Nineteenth Day of March, 1991

Attest:

HARRY F. MANBECK, JR.

Attesting Officer

Commissioner of Patents and Trademarks